(12) United States Patent
Rice et al.

(10) Patent No.: US 6,759,036 B1
(45) Date of Patent: Jul. 6, 2004

(54) FIBROCYTE-BASE VACCINE FORMULATIONS

(75) Inventors: Glenn C. Rice, Hillsborough, CA (US); Richard J. Bucala, Cos Cob, CT (US)

(73) Assignee: The Picower Institute for Medical Research, Manhasset, NY (US)

(*) Notice: Subject to any disclaimer, the term of this patent is extended or adjusted under 35 U.S.C. 154(b) by 0 days.

(21) Appl. No.: 08/828,415

(22) Filed: Mar. 28, 1997

(51) Int. Cl.⁷ .......................... A01N 63/00; A61K 48/00
(52) U.S. Cl. .................. 424/93.1; 424/93.2; 424/93.21; 424/93.7
(58) Field of Search .................. 435/325; 424/93.1, 424/93.2, 93.21, 93.7

(56) References Cited

U.S. PATENT DOCUMENTS 5,654,186 A * 8/1997 Cerami et al. .............. 435/325

OTHER PUBLICATIONS

Taber's Cyclopedic Medical Dictionary (C.C. Thomas Ed, 16ᵗʰEd F.A. Davis Co, Philadelphia, p. 669, 1989.*
Guo et al (Science, 263: 518–520), 1994.*
Koby (Immunology, W.H. Freeman & Co, NY p 242), 1994.*
Dictionary of Immunology, Herbert et al, Eds, 4ᵗʰ Ed. Academic Press, London, pp. 42–43, 1995.*

* cited by examiner

*Primary Examiner*—Susan Ungar
(74) *Attorney, Agent, or Firm*—Piper Rudnick LLP; Steven B. Kelber

(57) ABSTRACT

There is disclosed a fibrocyte-based vaccine formulations made from isolated fibrocytes. There is further disclosed a method for establishing an immune response against a specific antigen by administering a fibrocyte-based vaccine formulation, such as one made by pulsing fibrocytes in culture with the antigen peptide or protein, or by fusing tumor cells (whole cells or membrane fragments thereof) with fibrocytes.

4 Claims, 17 Drawing Sheets

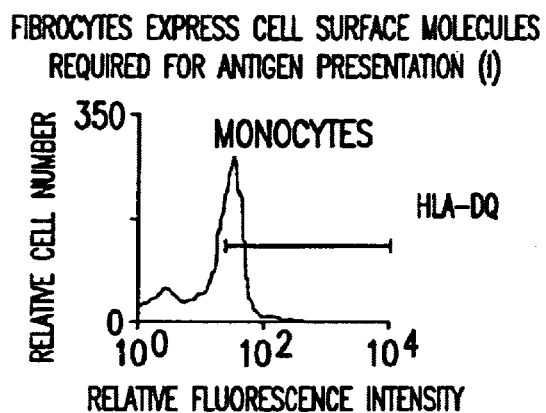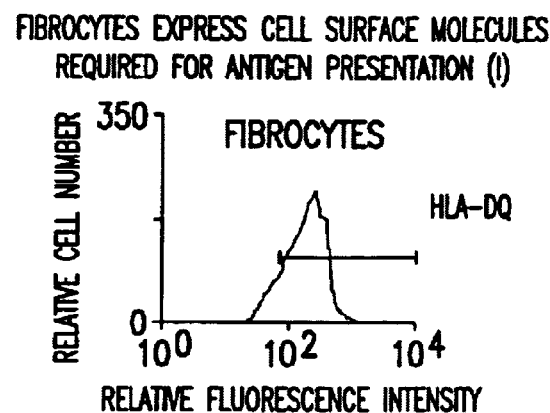
FIG.3G
FIG.3H
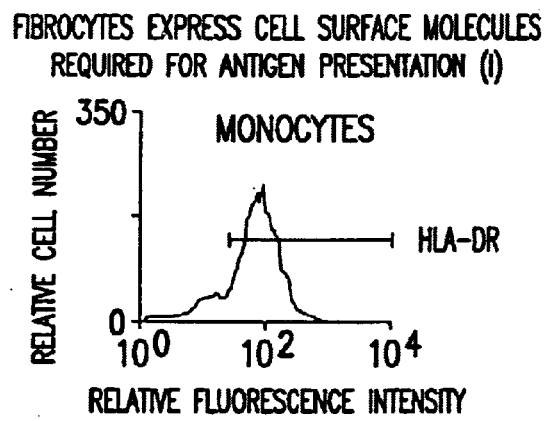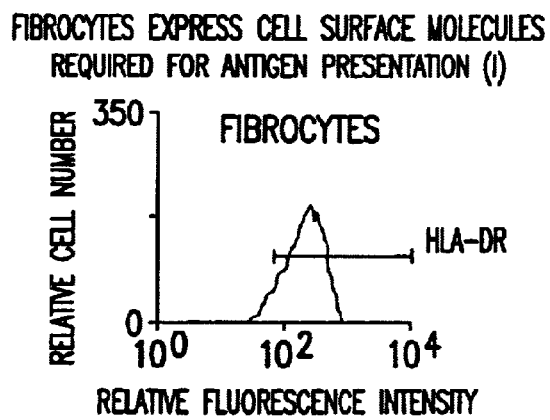
FIG.3I
FIG.3J

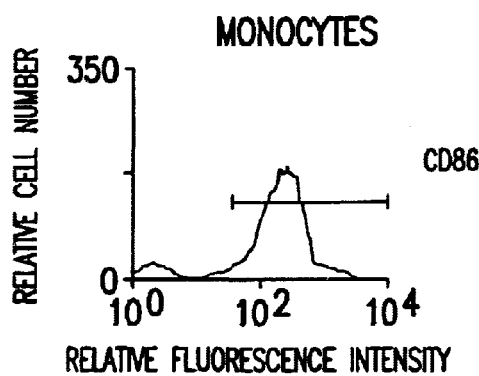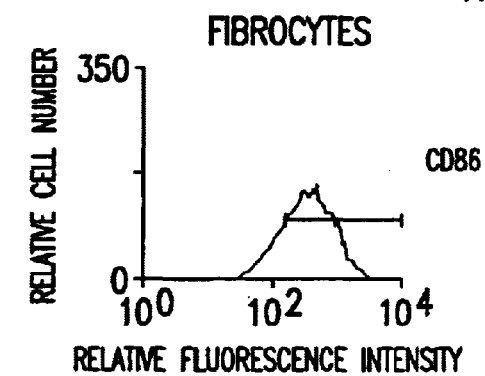
FIG.4G
FIG.4H

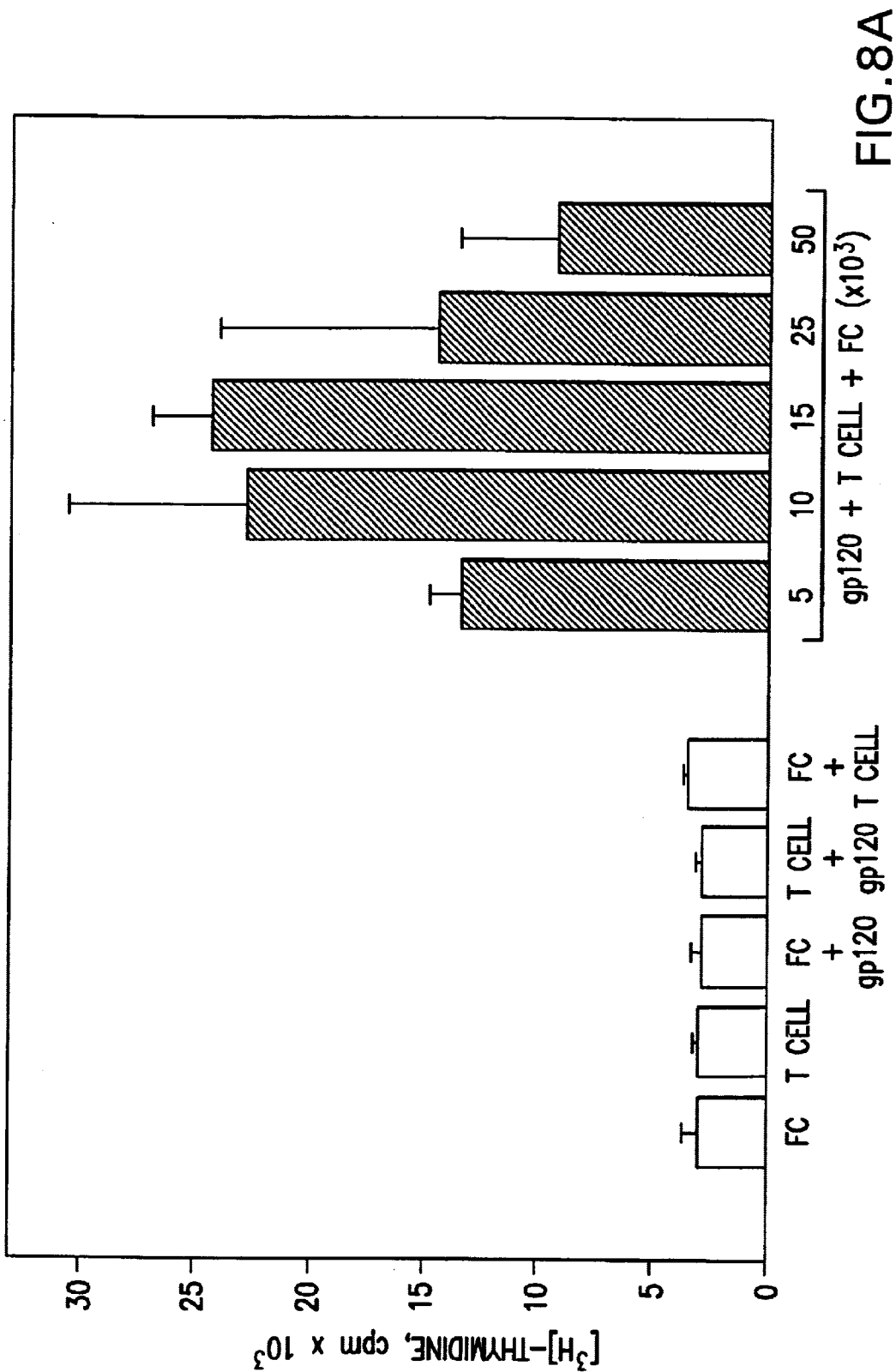

US 6,759,036 B1

FIBROCYTE-BASE VACCINE FORMULATIONS

TECHNICAL FIELD OF THE INVENTION

The present invention provides fibrocyte-based vaccine formulations made from isolated fibrocytes. The present invention further provides a method for establishing an immune response against a specific antigen by administering a fibrocyte-based vaccine formulation, such as one made by pulsing fibrocytes in culture with the antigen peptide or protein, or transfecting fibrocytes with genes encoding specific antigenic determinants of peptides or proteins, or by fusing tumor cells (whole cells or membrane fragments thereof) with fibrocytes.

BACKGROUND OF THE INVENTION

The immune response involves a) recognition of a specific antigen by a lymphocyte, b) elaboration of specific cellular and humoral effectors, leading to c) elimination of the antigen by specific effector cells such as T-lymphocytes and antibodies derived from B-cells, which mediate cellular and humoral immune responses, respectively. The cellular immune response begins with the recognition of antigen on the surface of an antigen-presenting cell (APC). Cellular antigen recognition is through a subset of lymphocytes called T-lymphocytes. T-lymphocytes include at least two functional subsets. These include T-helper lymphocytes (TH) that usually express the CD4 surface marker and cytotoxic T-lymphocytes (CTL) that usually express the CD8 surface maker. Both T-cell subsets express an antigen receptor that can recognize a given antigen, usually a peptide. The peptide, lipid or carbohydrate antigen needs to be associated with a major histocompatibility molecule (MHC) expressed on the surface of the APC. T-cells bearing the CD4 surface marker generally recognize antigens associated with MHC class II molecules. T-cells expressing the CD8 surface marker generally recognize antigens associated with MHC class I molecules.

In the case of protein antigens, a T-cell antigen receptor can only recognize peptides associated with MHC molecules at the surface of an APC. Thus, cellular proteins need to be processed into such peptides and transported with MHC molecules at the cell surface. This is referred to as "antigen processing." Exogenous proteins, phagocytosed by the APC, are broken down into peptides that are transported on MHC class II molecules to the cell surface where they can be recognized by CD4+ cells. In contrast, endogenous proteins synthesized by the APC are also broken down into peptides, but are transported by MHC class I molecules, where they are transported to the cell surface and recognized by CD8+ T-cells.

When a T-cell binds through its antigen receptor to its cognate peptide-MHC complex on the APC, the binding generates a first signal from the T-cell membrane towards its nucleus. However, this first signal is insufficient to activate the T-cell, at least as measured by induction of IL-2 synthesis and secretion. T-cell activation only occurs if a second signal or co-stimulatory signal is generated by the binding of other APC molecules to their appropriate receptors on the T-cell surface. The best known co-stimulatory molecules identified to date on APC are B7-1 and B7-2; both bind CTLA4/CD28 counter receptor on T-lymphocytes. In addition, adhesion molecules CD11a, CD54 and CD58 are thought to be important as co-stimulatory molecules. The ability to present peptide antigens together with co-stimulatory molecules in such a way as to activate T-cells is hereafter referred to as antigen presentation. Only APC's have the capacity to present antigens to $CD4^+$ (predominantly TH) and $CD8^+$ (predominantly CTL) T-cells, leading to the development of humoral and cellular immune responses.

Fibrocytes

APCs are heterogeneous in their cell lineage and functional properties. They include distinct cell types such as B-lymphocytes, T-lymphocytes, monocytes and macrophages, Langerhan cells and dendritic cells. A new isolated population of blood-borne fibroblast-like cells that rapidly enter sites of tissue injury, synthesize connective tissue matrix, and express fibrogenic cytokines (Bucala et al., *Mol. Medicine* 1:71–81, 1994) have been described. Termed "fibrocytes", these isolated cells can proliferate in culture, are adherent to culture plates, and display a spindle-shaped morphology. Fibrocytes have a distinct phenotype, characterized by surface markers, and synthesize the fibroblast products collagen I, collagen III and fibronectin and express several leukocyte-associated cell surface antigens, including CD45RO and the hematopoietic stem cell antigen CD34. Fibrocytes do not express a variety of endothelial, epithliial or smooth-muscle markers and are negative for non-specific esterases as well as the monocyte/macrophage specific markers CD4 and CD 16 (Bucala et al., 1994 infra.). Fibrocytes do not express CD25, a protein expressed constitutively by dendritic cells (Freudenthal and Steinman *Proc. Natl. Acad. Sci. USA* 87:7698–7702, 1990) or CD1a, a Langerhans cell marker (Chu and Jaffe, *Br. J Cancer Suppl.* 23:S4–S10, 1994). Thus, an isolated fibrocyte cell is a unique cell type with a defined phenotype readily distinguishable from other known APC types.

Fibrocytes expresses the cell surface molecules that are required for antigen presentation and are potent inducers of antigen-specific T-cell proliferation in vitro and in vivo. Isolated fibrocytes express high levels of class II MHC molecule HLA-DR. For example, mouse isolated fibrocytes, pulsed in vitro with foreign antigen and injected into the skin, were found to migrate to regional lymph notes and to prime T-cells. An example is shown pulsing fibrocytes with protein p120, both proteins expressed of HIV.

Immunohistochemical analyses of tissues undergoing fibrosis and tissue remodeling have identified fibrocytes to be present within areas of extracellular matrix deposition, providing direct evidence for the participation of fibrocytes in the host repair response to tissue injury (Bucala et al., 1994 infra.). Peripheral blood fibrocytes express a full complement of surface proteins required for antigen presentation, are potent stimulators of antigen-specific T cells in vitro, and migrate to lymph nodes and sensitize naive T cells in situ.

Fibrocytes also have been shown to secrete a number of inflammatory cytokines in vitro and are a particularly abundant source of the potent CD4+ T cell chemoattractants, macrophage inflammatory proteins (MIP-1α and 1β) (Schall et al., *J. Exp. Med.* 177:1821–1825, 1993). The entry of $CD4^+$ T cells into areas of tissue damage is considered to be an essential requirement for the generation of an antigen-specific immune response (Wahl and Wahl. in *Wound Healing: Biochemical and Clinical Aspects*, eds. Cohen et al. eds. Saunders Company, Philadelphia, 40–62, 1992). Fibrocytes thus may act to not only activate but to also recruit CD4+ T cells into the tissue repair micro-environment.

The constitutive expression by fibrocytes of the surface proteins known to be necessary for antigen presentation contrasts with what has been described for tissue fibroblasts which require activation by inteferon-γ to express measurable quantities of HLA-DR (Geppert and Lipsky, *J. Immunol.* 135:3750–3762, 1985). Although several tissue-derived cells have been shown to be capable of presenting antigen to memory T cells, including dermal fibroblasts, endothelial cells, and melanocytes (Pober et al., *J. Exp. Med.*, 157:1339–1353, 1983; and Le Poole et al., *J. Immunol.*, 151:12,7284–7292, 1993), sensitization of native T cells has been considered to be a particular function of dendritic cells (Inaba et al., *J. Exp. Med.* 172:631–640, 1990; and Levin et al., *J. Immunol.* 151:12,6742–6750, 1993). Fibrocytes also preset antigen to naive T cells but are distinct from dendritic cells and their precursors not only in their growth properties (fibrocytes are an adherent, proliferating cell population whereas dendritic cells are non-adhering and poorly proliferating) but also in their surface protein expression (collagen$^+$/CD13$^+$/CD34$^+$/CD25$^-$/CD10$^-$/CD38$^-$).

SUMMARY OF THE INVENTION

The present invention provides fibrocyte-based vaccine formulations made from isolated fibrocytes and an antigenic component, wherein the antigenic component is selected from the group consisting of pulsed antigen (protein, peptide, lipid, carbohydrate or a synthetic compound), a gene encoding specific antigenic determinants of proteins or peptides, tumor cells, and membrane fragments from tumor cells. Preferably, the antigenic component is a tumor cell or a tumor cell membrane that is fused with the isolated fibrocytes to form a fused cell that is the fibrocyte-based vaccine formulation. Preferably, the fusion process occurs ex vivo and the fibrocyte-based vaccine formulation is administered in vivo. Preferably the fibrocyte-based vaccine formulation is directed against an infectious disease and is formed by transfecting fibrocytes with a gene encoding a viral or a bacterial antigenic determinant that is displayed as an MHC class II antigenic determinant on the surface of the transfected fibrocytes.

The present invention further provides a method for establishing an immune response against a specific antigen by administering a fibrocyte-based vaccine formulation, such as one made by pulsing fibrocytes in culture with the antigen peptide or protein, or transfecting fibrocytes with genes encoding specific antigenic determinants of peptides or proteins, or by fusing tumor cells (whole cells or membrane fragments thereof) with fibrocytes. Preferably, the method provides an immune response is directed against a tumor antigen, a viral antigen, or a bacterial antigen. Preferably, the fibrocyte-based vaccine is produced by a process comprising pulsing fibrocytes in culture with an antigen peptide or protein, or transfecting fibrocytes with genes encoding specific antigenic determinants of peptides or proteins, or by fusing tumor cells (whole cells or membrane fragments thereof) with fibrocytes.

The present invention further provides a process for producing a fibrocyte-based vaccine formulation, comprising: (a) obtaining isolated fibrocytes, and (b) either (i) pulsing fibrocytes in culture with an antigen peptide or protein; or (ii) transfecting fibrocytes with genes encoding specific antigenic determinants of peptides or proteins; or (iii) fusing tumor cells (whole cells or membrane fragments thereof) with fibrocytes. Preferably, the fusion process (iii) is performed by mixing a population of isolated fibrocyte cells taken from a patient having cancer with tumor cells taken from the patient in a fusion catalyst, and isolating fused cells from non-fused fibrocytes or tumor cells by density gradient means to form a fibrocyte-based vaccine formulation. Most preferably, the process further comprises irradiating the isolated fibrocyte-based vaccine formulation to insure that it is incapable of growth after in vivo administration.

BRIEF DESCRIPTION OF THE DRAWINGS

FIGS. 8A and 8B show murine fibrocyte antigen presentation in vitro. $2 \times 10^5$ murine T cells purified from the spleens of p24 (A) or gp120 (B) immunized BALB/c mice were incubated with 2 mg/ml p24 or gp 120 together with various numbers of mitomycin C-treated autologous fibrocytes. After incubation for 5 days, the cultures were pulsed for 12 hours with 4 mCi/ml [$^3$H]thymidine and cell proliferation analyzed by liquid scintillation counting. Controls are illustrated on the left side of each figure. Data are expressed as mean±SD and are representative of one experiment that was performed three times.

DETAILED DESCRIPTION OF THE INVENTION

Fibrocyte-Based Vaccine Formulation

Figure 1:
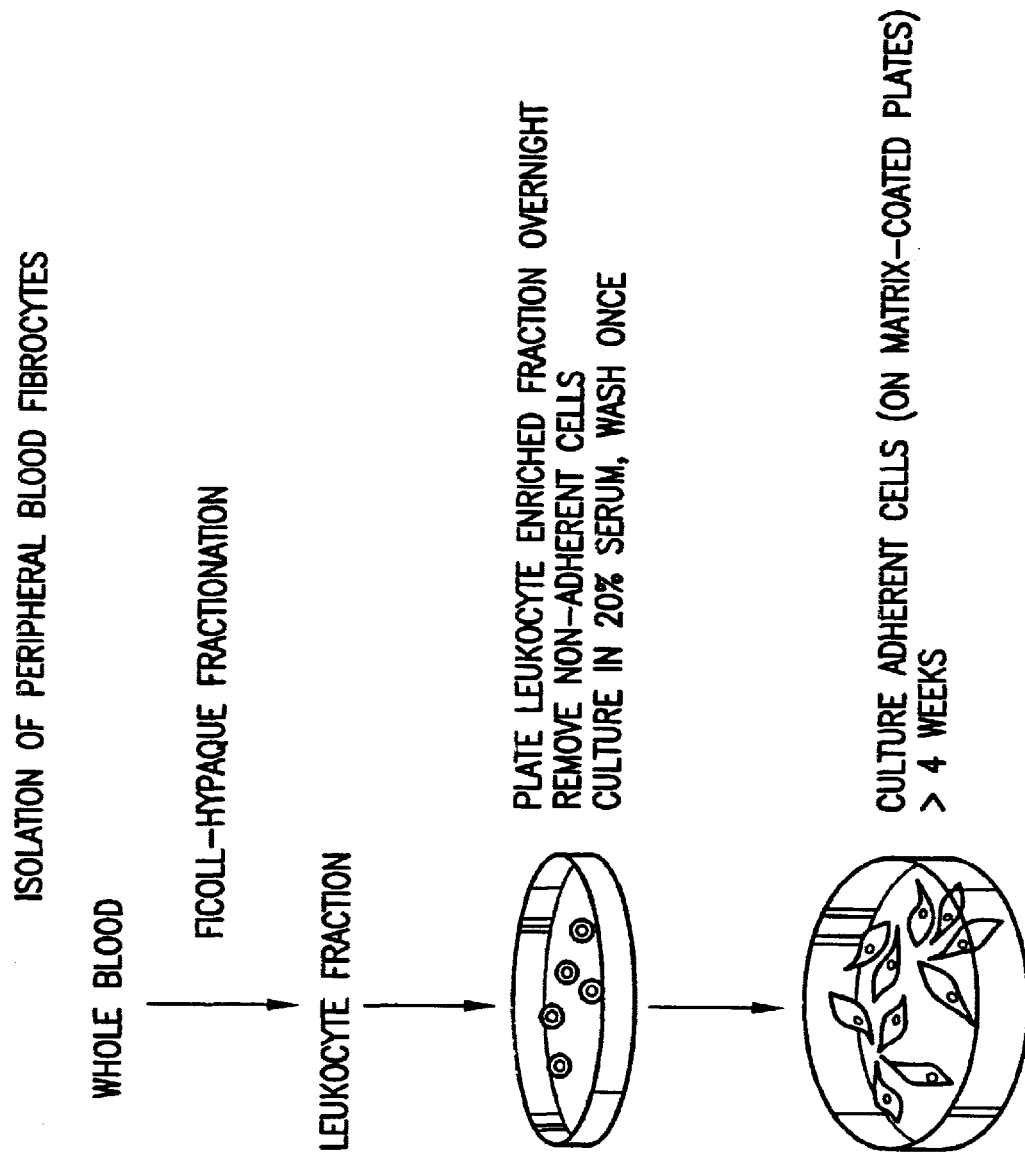
FIG. 1 shows a schematic of a method for isolating fibrocytes from peripheral blood. Approximately 50 ml of human whole blood (or 5–10 ml of murine whole blood) is utilized.

The present invention provides a fibrocyte-based vaccine formulation made from isolated fibrocytes and an antigenic component, wherein the antigenic component is selected from the group consisting of pulsed antigen (protein, peptide, lipid or carbohydrate), a gene encoding specific antigenic determinants of proteins or peptides, tumor cells, and membrane fragments from tumor cells. Preferably, the antigenic component is a tumor cell or a tumor cell membrane that is fused with the isolated fibrocytes to form a fused cell that is the fibrocyte-based vaccine formulation. Preferably, the fusion process occurs ex vivo and the fibrocyte-based vaccine formulation is administered in vivo. Preferably the fibrocyte-based vaccine formulation is directed against an infectious disease and is formed by transfecting fibrocytes with a gene encoding a viral or a bacterial antigenic determinant that is displayed as an MHC class II antigenic determinant on the surface of the transfected fibrocytes.

Fibrocytes are potent antigen presenting cells that prime native cytotoxic T cells (CTLs). Fibrocytes are produced by a process for isolating fibrocyte cells from peripheral blood. Briefly, peripheral blood mononuclear cells (PBMCs) were isolated from human blood by centrifugation over a commercial density gradient (Ficoll-Paque® Pharmacia, Uppsala, Sweden) following the manufacturer's procedures. The isolated PBMCs were cultured overnight on either non-coated ("Control") or fibronectin-coated plastic (6-well, 5×10$^6$ PBMCs/well) plates (both from Becton Dickenson Labware, Bedford, Mass.) in Dulbecco's Minimal Eagle Medium (Life Technologies, Gaithersberg, Md.) supplemented with 20% fetal bovine serum (Hyclone Labs, Logan, Utah). The non-adherent cells were removed by a single, gentle aspiration.

The cultures were incubated for ten days in continuous culture. The adherent cells were lifted by incubation in cold 0.05% EDTA (Sigma, St. Louis, Mo.) in phosphate buffered saline (PBS, Life Technologies) and analyzed for fibrocytes by flow cytometry. Cell samples (2×10$^5$ cells/sample) were washed twice in PBS containing 0.1% by weight sodium azide (Sigma) and 1% by weight bovine serum albumin (Sigma) (FACS medium). The cells were incubated for 30 minutes on ice in 25 µl of FACS medium containing the following antibodies: phycoerythrin-conjugated anti-CD34 monoclonal antibody (Becton Dickenson) and fluorescein-conjugated anti-collagen I mAb (Chemicon, Temecula, Calif.). The cells were then washed twice in PBS and then resuspended in 200 µl of FACS medium. At least 100,000 cells were analyzed on a FACScan instrument (Becton Dickenson). Cell viability was determined by trypan blue exclusion.

The isolated fibrocytes are fused with tumor cells or tumor cell membranes displaying appropriate tumor antigens. Standard fusion methods, such as those used for hybridoma fused cells are used. Briefly, one method mixes the cells in flasks in 50% PEG (polyethylene glycol) in Dulbecco's phosphate buffered saline without Ca2+ or Mg2+ at pH 7.4. The fused cells were then plated in 24-well culture plates in the presence of HAT selection medium (Sigma) for 10–14 days.

Another method for forming fusion cells is to fuse the isolated fibrocytes with tumor cells or tumor cell membrane fragments is to mix the cell again in PEG for several days in culture, waiting for unfused fibrocytes cells to die off to better isolate a population of fused fibrocytes. The fused fibrocyte cells are separated from the unfused tumor cells by switching to HAT medium with aminopterin to prevent cells from making their own thymidine. The fused cells will grow well in this medium and double in every 1–4 days, whereas the tumor cells should die off. Thus, the surviving cells should be a fairly homogenous population of fused fibrocyte cells.

When fibrocytes are fused with tumor cells or tumor cell membranes displaying tumor antigens, the fused cells are positive for MHC class I and class II antigens. In an experiment showing the utility of the claimed invention, fibrocytes were fused with MC38 carcinoma cells which express the DF3/MUC1 tumor-associated antigen. The results show that the fusion cells stimulated native T cells in a primary mixed lymphocyte reaction (MLR) and induced MC38/MUC1 tumor specific CTLs in vivo. Antibody-mediated depletion experiments demonstrated that induction of CD4+ and CD8+ CTLs protected against challenge with tumor cells, and immunization with the inventive fusion cells induced rejection of established metastases, indication the therapeutic utility of he inventive fusion cells for treating established cancers. Therefore, the inventive fibrocytes fused with tumor cells or tumor cell membranes are effective as tumor vaccines for treating or preventing cancer.

Fibrocytes are fused with tumor cells to form a fused fibrocyte/tumor cell and the fused fibrocyte/tumor cells isolated, cultured and utilized as a tumor immunogen. For example, murine MC38 adenocarcinoma cells that stably express the marker DF3/MUC1 antigen were fused to peripheral blood derived fibrocytes. Cells were maintained in DMEM supplemented with 10% heat-inactivated fetal calf serum (FCS), 2 mM glutamine, 100 U/ml penicillin and 100 µg/ml streptomycin. Fusion efficiencies may be enhanced by pre-culturing tumor cells and fibrocytes prior to fusion as well as fusing at relatively low cell densities (<10$^6$/ml). However, fusion at low cell densities is not a requirement for fusion. Agents that act to enhance fiboryc-te:tumor cell adherence also enhance fusion efficiencies. These agents include, for example, IL-1α and IL-1β. In addition, a fibrocyte may be modified prior to fusion with a tumor cell to increase the immuno-potency of the resultant hybrid. This modification can take several different means, including gene or protein transfer. Examples of proteins that can be expressed or inhibited in a fibrocyte include cytokines, chemokines, adhesion receptors, or co-stimulatory molecules.

Fibrocytes were isolated as described above. The cells were plated in six-well culture plates in RPMI medium supplemented with 20% FCS. Fusion was carried out with 50% PEG in Dulbecco's phosphate buffered saline without $Ca^{2+}$ or $Mg^{2+}$ at pH 7.4. The fused fibrocyte/tumor cells were plated in 24 well culture plates in the presence of HAT selection medium (Sigma) (100 $\mu$M hypoxanthine, 0.8 $\mu$M aminopterine, and 16 $\mu$M thymidine) for 10–14 days. Other methods of fusion are also applicable, including other chemical means, varying the electric strength such is in electroporation and by alterations in external atmospheric pressure.

Method for Establishing an Immune Response

The present invention further provides a method for establishing an immune response against a specific antigen by administering a fibrocyte-based vaccine formulation, such as one made by pulsing fibrocytes in culture with the antigen peptide or protein, or transfecting fibrocytes with genes encoding specific antigenic determinants of peptides or proteins, or by fusing tumor cells (whole cells or membrane fragments thereof) with fibrocytes. Preferably, the method provides an immune response is directed against a tumor antigen, a viral antigen, or a bacterial antigen. Preferably, the fibrocyte-based vaccine is produced by a process comprising pulsing fibrocytes in culture with an antigen peptide or protein, or transfecting fibrocytes with genes encoding specific antigenic determinants of peptides or proteins, or by fusing tumor cells (whole cells or membrane fragments thereof) with fibrocytes.

The exemplary fused fibrocyte/tumor cells, made according to the method described above, express DF3/MUC1 as well as class II and other co-stimulatory molecules. Injection of MC38/MUC1 cells in mice resulted in the formation of subcutaneous tumors. Similar findings were obtained with MC38/MUC1 cells mixed with fibrocytes. However, no tumors formed in mice injected with fused MC38/MUC1/fibrocyte cells and fibrocytes. These data show the therapeutic utility of a fibrocyte fusion cell over an unfused fibrocyte cell when used for autologous treatment of tumors.

Mice were immunized twice with fused MC38/MUC1/fibrocytes cells and fibrocytes to assess function in vivo. All animals remained tumor free after challenge with $2.5 \times 10^5$ to $2 \times 10^6$ MC38/MUC1 cells. Control animals immunized with fibrocytes alone or PBS and then challenged subcutaneously with $2.5 \times 10^5$ MC38/MUC1 cells exhibited tumor growth within 10–20 days. CTL's isolated from mice immunized with fibrocytes or PBS exhibited no detectable lysis of the MC38/MUC1 targets. However CTL's isolated from mice immunized with the fibrocyte/tumor fusion cells induced lysis of the MC38/MUC1 cells.

A model of MC38/MUC1 pulmonary metastases was used to determine whether immunization with fibrocyte/tumor fused cells is effective for the prevention of disseminated disease. Immunization with the fibrocyte/tumor fused cells intravenously or subcutaneously completely protected against intravenous challenge with MC38/MUC1 cells. By contrast, all non-immunized mice similarly challenged with MC38/MUC1 cells developed over 250 pulmonary metastases. In a treatment model, MC38/MUC1 pulmonary metastasis were established 4 days prior to immunization with fused fibrocyte/tumor cells. Control mice, treated with vehicle, developed over 250 metastases. Treated mice on the other hand had none.

The present invention discloses the capacity of a fibrocyte/tumor fusion cell to stimulate anti-tumor responses and T-cells. This capacity can be used for both in vivo and ex vivo stimulation of T-cells. Ex vivo stimulation of a T cell using a fibrocytes/fusion product can be used as a means of amplifying T-cells with a tumor specificity prior to infusion of such T-cells into patients. Methods are well known in the art for delivering T-cells into patients.

The fused fibrocyte/tumor fusion cells may be used either in a prophylactic or treatment procedure generally with autologous but also allogeneic procedures. The use of fusion with fibrocytes provides substantial advantages for practicing tumor cell engineering and enhancing tumor cell immunogenicity. There is no need for decoding the precise tumor antigens that may be expressed in the particular tumor. Cell fusion is applicable to diverse tumor types, including solid and blood tumors. It is a simple process and can utilize fusion methods involving chemical fusion, or methods of generating cell fusion that involve electric fields or high pressure. The tumor cell contributes relevant tumor-specific antigens to the hybrid cell or membrane preparation and the fibrocyte-like cell contributes cell surface co-stimulators, soluble cytokines, MHC molecules, adhesion molecules, chemokines and other undefined molecular factors to the hybrid cell. This results in a highly antigenic and immunogenic phenotype for the hybrid cell or hybrid cell membrane preparations. In turn, the hybrid cell can be used as an effective cellular vaccine.

The present invention is, in part, based upon the finding that enhanced immunogenicity can be induced by fusing a cell membrane from a tumor cell with a cell membrane from a fibrocyte or an isolated population of fibrocyte cells. The resulting a fibrocyte-tumor cell fusion is shown to stimulate anti-tumor T-cells and to have significant anti-tumor activity in relevant animal tumor models. Through such fusion the full complement of molecular factors that are normally produced by professional APC's and that are required for effective T-cell activation are combined with a full set of potential tumor antigens associated with a particular tumor.

Fibrocyte-Based Vaccines Made by A Transfection Process

This invention also provides a fibrocyte-vaccine formulation wherein the antigenic component is a pulsed antigen protein or peptide, or a gene encoding specific antigenic determinants of proteins or peptides for uses in tumor immunotherapy. Fibrocytes can be induced in vitro to secrete, for example, tumor antigens, viral markers, or T-cell attractants in vivo for enhanced immunogenicity. These T-cell attractants include, for example, various chemokines, cell surface proteins and secreted cytokines. For instance, IL-1$\beta$ can induce fibrocyte expression of MIP-1$\alpha$, a powerful T-cell chemoattractant. IL-1$\beta$ also induces fibrocyte migration which is important for T-cell interaction with the fibrocyte.

Fibrocytes may be used for generating immune response against specific antigens not only involved in viral, but also bacterial, fungal and parasitic infections. In another approach, fibrocytes may be loaded with a source of tumor antigen. Where aberrant expression of specific antigen is known, this approach is useful for generating immune responses against specific tumors. Tumor specific antigens which may be used in peptide pulsing of fibrocytes for tumor immune therapy may include, but are not limited to, MAGE, CEA, PSA, Her2/neu, and other tumor derived peptides (Wang and Rosenberg, *J. Leuk. Biol.* 60:296–309, 1996).

Alternatively, fibrocytes may be transfected with the genes encoding such tumor derived peptides.

This method is useful for more standard ex vivo immunotherapy protocols, such as tumor peptide or protein "pulsing" of fibrocytes. However, with the tumor-fibrocyte fusion there is no requirement for identification of tumor specific antigens, nor the production and purification of the corresponding recombinant proteins. In addition, tumor antigens are displayed in a more physiological state, within a cellular membrane.

Process for Producing a Fibrocyte-Based Vaccine Formulation

The present invention further provides a process for producing a fibrocyte-based vaccine formulation, comprising: (a) obtaining isolated fibrocytes, and (b) either (i) pulsing fibrocytes in culture with an antigen peptide or protein; or (ii) transfecting fibrocytes with genes encoding specific antigenic determinants of peptides or proteins; or (iii) fusing tumor cells (whole cells or membrane fragments thereof) with fibrocytes. Preferably, the fusion process (iii) is performed by mixing a population of isolated fibrocyte cells taken from a patient having cancer with tumor cells taken from the patient in a fusion catalyst, and isolating fused cells from non-fused fibrocytes or tumor cells by density gradient means to form a fibrocyte-based vaccine formulation. Most preferably, the process further comprises irradiating the isolated fibrocyte-based vaccine formulation to insure that it is incapable of growth after in vivo administration.

Advantage of Fibrocytes Versus Dendritic Cells

Use of the fibrocyte for tumor, viral, fungal, bacterial or parasitic immunization has distinct advantages over the use of other APCs (antigen presenting cells). First, unlike dendritic cells, fibrocytes can be conveniently separated from blood and the separation involves straightforward means, without the need for complicated selection, such as a selection based on the CD34 antigen. Second, fibrocytes constitute upwards to 0.3% of the circulating PBL's, a frequency much higher than dendritic cells. Third, fibrocytes are potent APCs, at least equivalent to dendritic cells and superior to monocytes. Fourth, fibrocytes do not require sophisticated and complex cocktails of cytokines and growth factors (such as GM-CSF, IL-3, TNF, IL-1 Flt-3, etc.) for ex vivo expansion, as required for dendritic cells and other APCs. Fifth, fibrocytes (unlike dendritic cells) divide with rapid doubling times ex vivo, which allows for harvesting large numbers of cells useful for immunotherapy and allowing cell banking of fibrocytes for later use.

EXAMPLE 1

This example illustrates a process for isolation, characterization and culturing of isolated fibrocytes for use with the present inventive methods and products. For murine studies BALB/c ($H-2^d$), DBA-2 ($H-2^d$), C3H/HeJ ($H-2^k$), and DBA-2×C3H/HeJ ($H-2^{d \times k}$) mice of both sexes were purchased from The Jackson Laboratory, Bar Harbor, Me. Fibrocytes were harvested and cultured as previously described (Bucala et al., *Mol. Medicine* 1, 71–81, 1994). Briefly, PBMCs were isolated from human or murine blood by centrifugation over Ficoll-Paque (Pharmacia, Uppsala, Sweden) following the manufacturer's protocol. After overnight culture on fibronectin-coated plates (human; 6-well plates, $5 \times 10^6$ PBMCs/well, murine; 24-well plates, $3 \times 10^6$ PBMCs/well) (Becton Dickinson Labware, Bedford, Mass.) in DME medium (Life Technologies, Gaithersburg, Md.) supplemented with 20% FCS (Hyclone Labs, Logan, Utah), the nonadherent cells were removed by a single, gentle aspiration. Following 10 days of continuous culture, the adherent cells were lifted by incubation in cold 0.05% EDTA (Sigma, St. Louis, Mo.) in PBS (Life Technologies) and were depleted by immunomagnetic selection of contaminating T cells (human: Dynabeads M-450 pan-T, anti-CD2; murine: pan-T, anti-CD90, Dynal, Lake Success, N.Y.), monocytes (human: Dynabeads M-450 anti-CD14; murine: Dynabeads M-450 sheep anti-rat IgG, Dynal, anti-CD14, rat $IgG_1$, clone rmC5-3, Pharmingen, San Diego Calif.), and B cells (human: Dynabeads M-450 Pan-B, anti-CD19; murine: pan-B, anti-B220, Dynal). Fibrocyte purity was verified to be >95% (70–80% prior to depletion of contaminating cells) by flow cytometry analysis (described below) using both phycoerthrin-conjugated anti-CD34 monoclonal antibody (mAb) (Becton Dickinson) and fluorescein-conjugated anti-collagen I mAb (Chemicon, Temecula, Calif.) (Bucala et al. 1994 infra.). Cell viability was determined to be >90% by Trypan Blue exclusion. For comparison, dendritic cells and monocytes were prepared using methods previously described (Bhardwaj et al., *J. Clin. Invest.* 94, 797–807, 1994; Bender et al., *J. Exp. Med.* 182:1663–1671, 1995). The overall scheme for isolation of fibrocytes is shown in FIG. 1.

For a flow cytometry analysis, $2 \times 10^5$ cells/sample were washed twice in PBS containing 0.1% sodium azide (Sigma) and 1% bovine serum albumin (Sigma) (FACS medium). The cells were resuspended in 25 ml of diluted antibody (in PBS) and incubated for 30 minutes on ice (Loken and Wells in *Flow Cytometry*, Ormeron ed., Oxford University Press, Oxford, 67–92, 1994). The cells then were washed twice in PBS and resuspended in 200 ml of FACS medium. At least 10,000 cells were analyzed on a FACScan instrument (Becton Dickinson). Human cells were stained with the following phycoerythrin or fluorescein-conjugated mAbs: anti-CD11a (clone G-25.2), anti-CD54 (clone LB-2); anti-CD58 (clone L306.4); anti-CD80 (clone L307.4) (each from Becton Dickinson); and anti-HLA-DP (clone HI43); anti-HLA-DQ (clone TU 169); anti-HLA-DR (clone TU36); and anti-CD86 (clone IT2.2) (each from Pharmingen, San Diego, Calif.). Murine fibrocytes were stained with the following phycoerythrin or fluorescein-conjugated mAbs: anti-I-$A^d$ (clone AMS-32.1); anti-CD11a (clone M17/4); anti-CD54 (clone 3E2); anti-CD86 (clone GL1) (each from Pharmingen); and anti-I-$E^d$ (clone E-E-D6) (Accurate, Westbury, N.Y.). Directly-conjugated isotype controls and cell only samples were analyzed with each antibody.

Figure 2B:
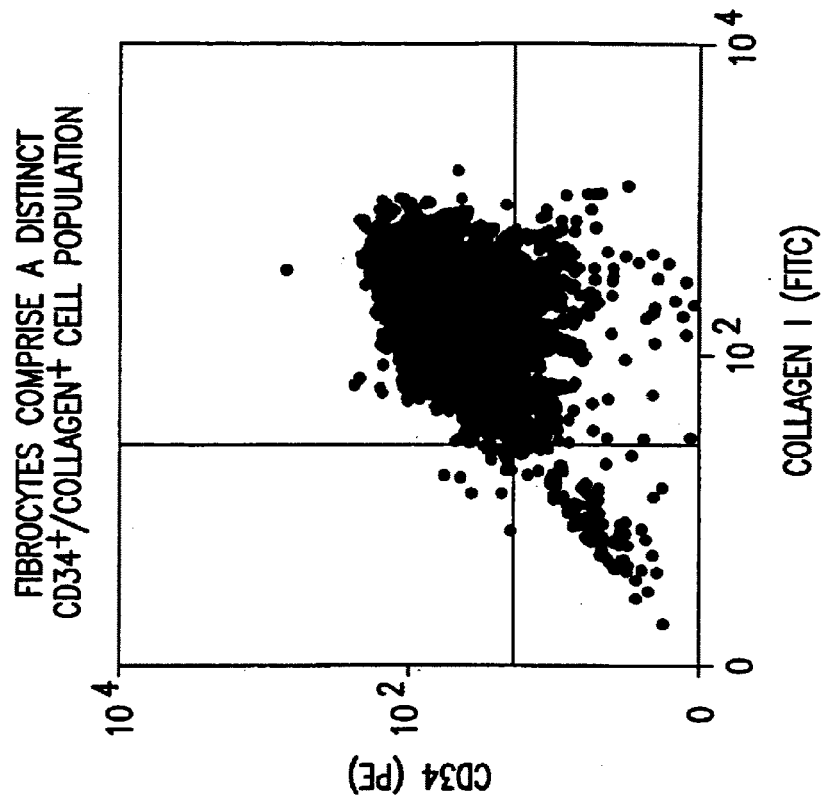
FIG. 2 shows the phenotype of the isolated fibrocytes, showing fibrocyte expression of CD34 and collagen I by flow cytometry.
Figure 2A:
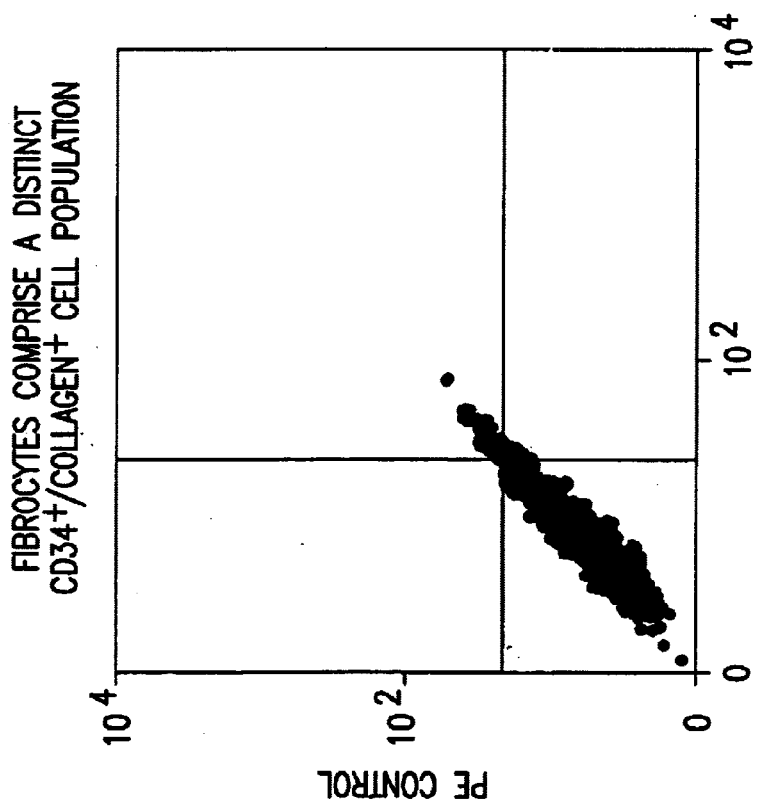
Figure 3A:
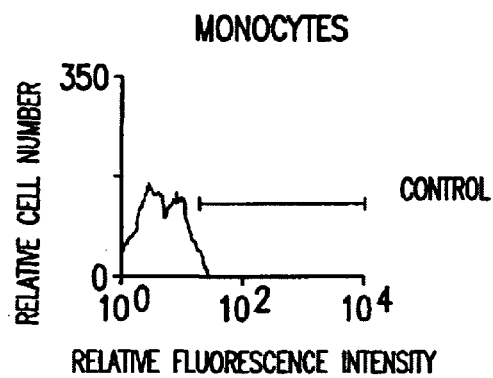
FIGS. 3 and 4 show flow cytometric analysis of various cell surface molecule expression (as indicated) in fibrocytes and a comparison to monocytes. The horizontal line in each panel marks fluorescence intensity greater than the background staining that was observed with an isotype control mAb (monoclonal antibody).
Figure 3B:
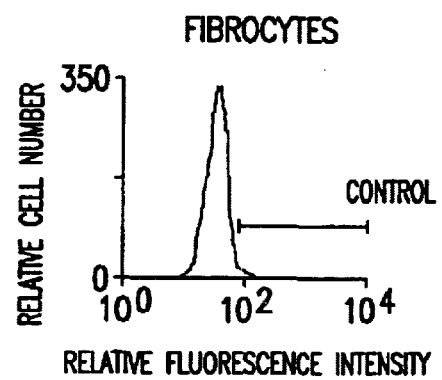
Figure 3C:
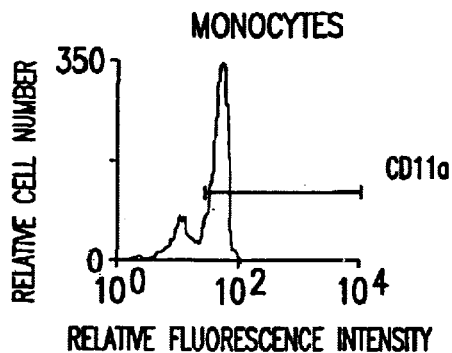
Figure 3D:
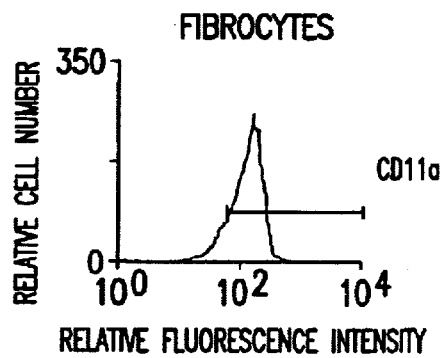
Figure 3E:
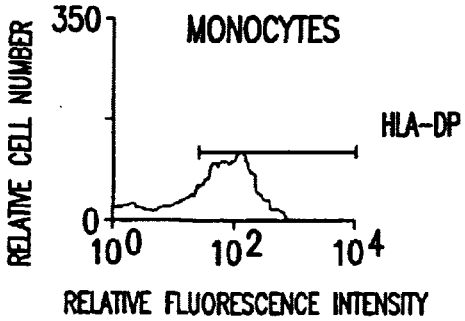
Figure 3F:
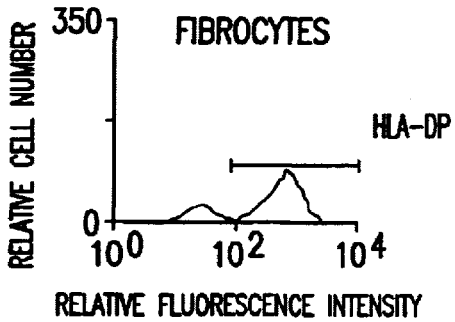
Figure 4A:
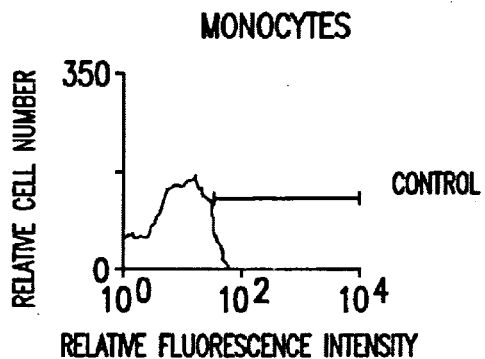
Figure 4B:
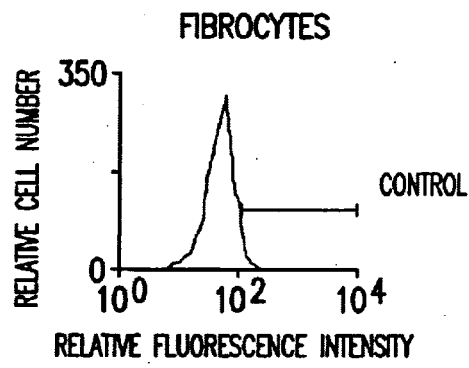
Figure 4C:
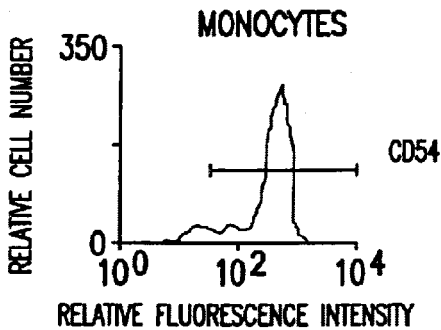
Figure 4D:
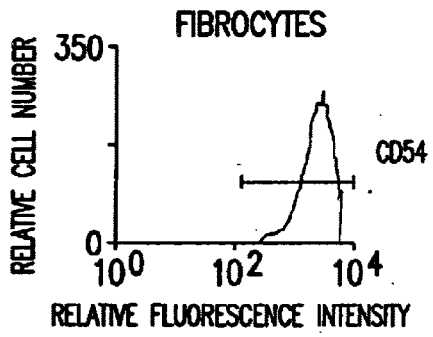
Figure 4E:
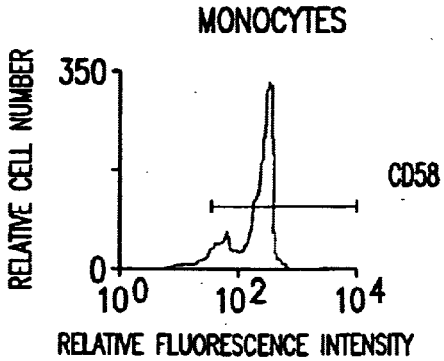
Figure 4F:
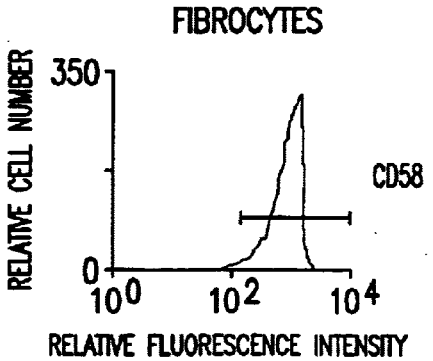

As shown in FIGS. 2–4, fibrocytes are unique among connective tissue cells in that they express collagens but circulate in blood and display the hematopoietic/leukocyte cell surface markers CD34 and CD45RO. Fibrocytes do not express epithelial (cytokeratin), endothelial (von Willebrand factor VII-related protein) or smooth muscle (α actin) cell markers and are negative for non-specific esterases as well as the monocyte/macrophage specific markers CD14 and CD16.

Antigen presenting cells are known to express cell surface proteins that enhance T cell stimulation in response to the MHC-peptide complex (reviewed in Clark and Ledbetter *Nature* 367:425–428, 1994). Specific receptor:co-receptor pairs which have been found to be essential include CD11a/18-CD54, CD58-CD2, and CD86-CD28. To characterize the ability of human fibrocytes to activate T cells, we first examined the expression of these molecules on the surface of purified, human fibrocytes. As shown in FIGS. 3 and 4, fibrocytes isolated from peripheral blood expressed high levels of the adhesion molecules, CD11a, CD54, and CD58. The level of expression is similar to that observed in purified, peripheral blood monocytes that had been cultured for 36 hours. Fibrocyte expression of the class II MHC molecules HLA-DP and HLA-DQ is higher in fibrocytes than in monocytes, although the expression of HLA-DR appears equivalent in both cell types. Fibrocytes express the co-stimulatory molecule CD86 (B7-2) at a level similar to that of monocytes. Fibrocytes also weakly express the co-stimulatory molecule CD80 (B7-1). These data indicate that fibrocytes constitutively produce the full complement of surface proteins that have been shown in other cell types to be necessary for antigen presentation.

EXAMPLE 2

This example illustrates a comparison of the antigen presenting qualities of fibrocytes to be approximately equivalent to dendritic cells. Various concentrations of mitomycin C-treated fibrocytes were co-cultured with allogeneic T cells for 96 hours and the T cell proliferative activity assessed by the incorporation of [$^3$H]thymidine into DNA. Fibrocytes were found to induce a significant T cell activation response ($5 \times 10^3$ fibrocytes+$2 \times 10^5$ T cells=70,321±10, 111 cpm, versus <300 cpm for T cells or fibrocytes alone, n=3 experiments, P<0.001).

The fibrocytes were examined for their capacity to present soluble antigen in an autologous, T cell proliferation assay. T cells were purified from the peripheral blood of tetanus toxoid-immunized individuals and stimulated with tetanus toxoid in vitro together with fibrocytes as APCs. To assess the functional capacity of fibrocytes to present antigen, we examined the ability of purified human fibrocytes to activate allogeneic T cells in a mixed leukocyte reaction. Three human blood donors were boosted intramuscularly with 4 units of tetanus toxoid (Connaught Laboratories, Swiftwater, Pa.). One month later, the PBMCs were isolated from the pheripheral blood. T cells were isolated by high-affinity negative selection (human T Cell Enrichment Column, R&D Systems, Minneapolis, Minn.). FACS analysis of anti-CD3 (Pharmingen) labeled cells indicated that 85–95% of all cells recovered were CD3$^+$. APCs were prepared as described above and treated with 25 mg/ml mitomycin C (Stigma) in RPMI medium containing 10% human AB serum (RPMI/ 10% HS) for 30 minutes and then washed 5 times with RPMI/10% HS. For each assay, the T cells ($2 \times 10^5$) were incubated with mitomycin C-treated autologous fibrocytes, monocytes, or dendritic cells at various T cell:APC ratios in the presence of 2 mg/ml tetanus toxoid in RPMI/10% HS (James, in *Current Protocols in Immunology* Coligan et al. eds. John Wiley and Sons, Inc. New York pp. 7.10.1–7.11.4, 1991). After 4, 5 and 6 days of co-culture, the proliferative activity was measured over 12 hours by the incorporation of [$^3$H]thymidine (4 mCi/ml) into DNA as measured by liquid scintillation counting. Controls that were included in each experiment were APCs alone, T cells alone, APCs+tetanus toxoid, T cells+tetanus toxoid, and APC+T cells. Mixed leukocyte reactions were conducted similarly except that the fibrocytes and T cells were isolated from allogenic donors and no antigen was included in the co-culture James 1991, infra.) Statistical significance as assessed by two sample T-tests (assuming unequal variances) (Zar, in *Biostatistical Analysis*, Prentice Hall, Engelwood Cliffs, N.J., pp. 176–179, 1984)

Figure 5A:
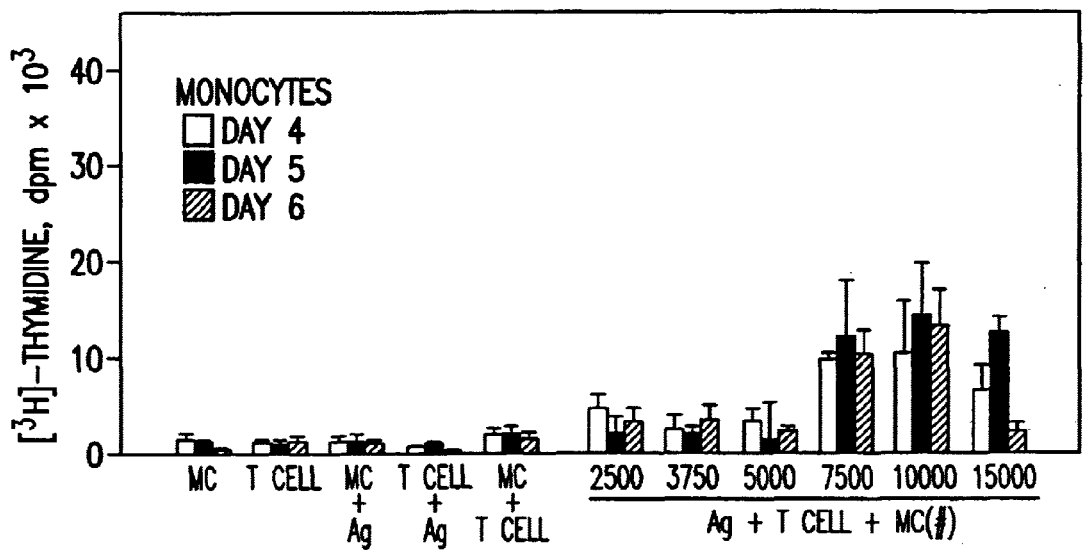
FIG. 5 provides a functional comparison of human fibrocyte, monocyte, and dendritic cell antigen presentation in vitro. $2 \times 10^5$ human T cells purified from a tetanus toxoid-immunized individual were incubated with 2 mg/ml tetanus toxoid together with various numbers (#) of autologous fibrocytes (A), autologous monocytes (B), or autologous dendritic cells (C). After incubation for 4 (first bar), 5 (second bar), and 6 (third bar) days, the cultures were pulsed for 12 hours with 4 mCi/ml [$^3$H]thymidine and cell proliferation analyzed by liquid scintillation counting. Controls are illustrated on the left side of each figure: APCs alone (FC=fibrocytes, MC=monocytes, DC=dendritic cells), T cells alone, APCs+Ag (tetanus toxoid), T cells+Ag (tetanus toxoid), and APCs+T cells. Data are expressed as mean±SD and are representative of one experiment that was performed three times.
Figure 5B:
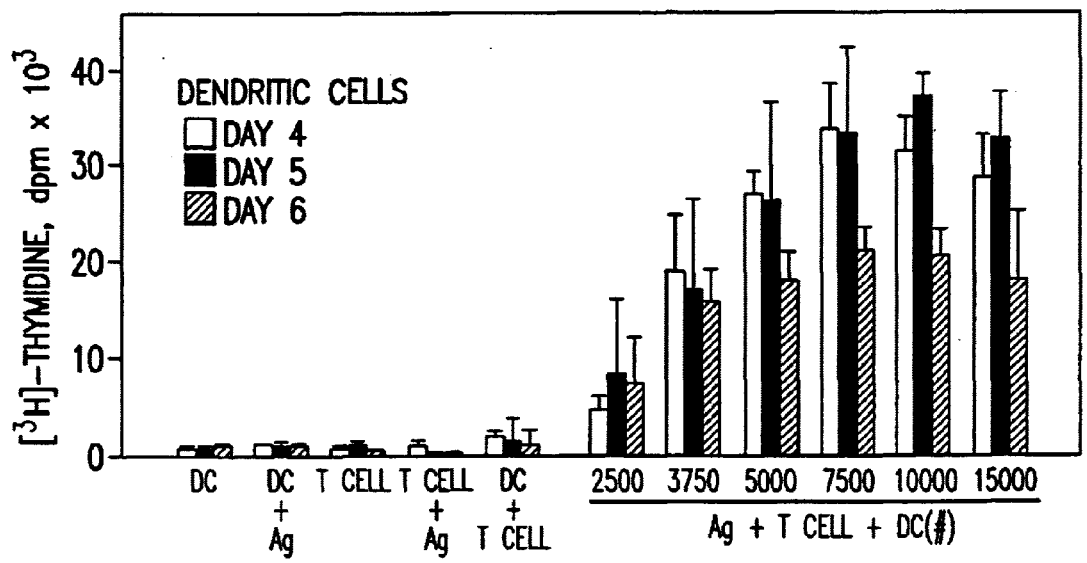
Figure 5C:
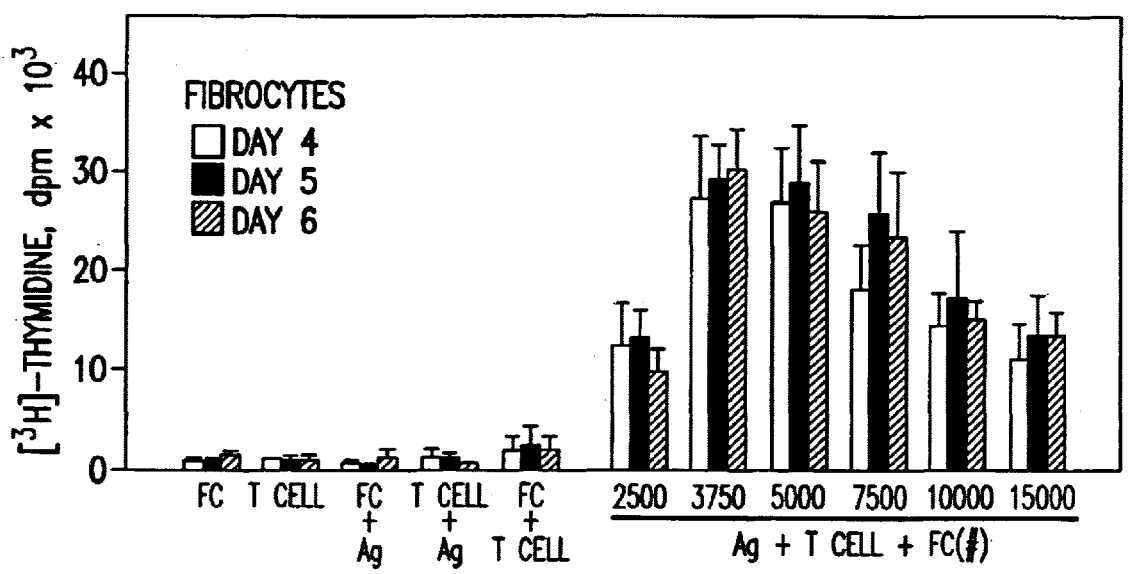

As shown in FIG. 5, mitomycin C-treated fibrocytes induced a powerful, antigen-dependent T cell proliferative response when co-incubated with autologous T cells. T cell proliferation, as measured by [$^3$H]thymidine incorporation, was greatest when 3750 fibrocytes were co-incubated with $2 \times 10^5$ T cells (30,475±3692 cpm). The level of T cell activation was not significantly different on days 4, 5, or 6 after the start of the co-incubation. Fixation of fibrocytes with paraformaldehyde prior to co-incubation with T cells and tetanus toxoid did not induce antigen-dependent proliferation (1050±378 cpm, 3750 fibrocytes+$2 \times 10^5$ T cells.

For comparison purposes, we also examined the antigen presenting capacity in vitro of two other purified cell types: monocytes and dendritic cells (FIG. 5). For the isolation of human dendritic cells, T cells first were depleted from PBMCs by rosetting with neuraminadase-treated sheep erythrocytes (Cocalico, Reamstown, Pa.) (see Bhardwaj et al., *J. Exp. Med.* 178:633–642, 1993). The T-depleted mononuclear cells were cultured in RPMI medium supplemented with 5% human AB serum (6102; Biocell, Rancho Dominquez, Calif.) for 2 days and the adherent cells (i.e. monocyte enriched) separated from the non-adherent cells. The adherent monocytes then were lifted from culture wells by incubation in cold PBS/0.5% EDTA and counted. The non-adherent cells were depleted of contaminating monocytes by adherence to human gamma globulin-coated petri dishes (Calbiochem-Behring Corp.) (Young and Steinman, *Cell. Immunol.* 111: 167–182, 1988). The remaining non-adherent cells then were layered onto 14% metrizamide gradients, centrifuged, and the low-density interface (which contains the dendritic cells) was collected. The dendritic cells were washed twice with PBS, enumerated (purity>70%), and cultured for further studies.

Using the same preparation of purified, autologous T cells, the peak antigen-dependent T cell proliferation response induced by monocytes was significantly lower than that induced by fibrocytes (14,555±5404 cpm, P<0.005). Furthermore, more monocytes than fibrocytes (10,000 monocytes versus 3750 fibrocytes) were required to reach maximum stimulation in the co-incubation assay.

The peak antigen-dependent T cell proliferation induced by dendritic cells was higher than that induced by fibrocytes (37,348±2019 cpm, P<0.01). However, more dendritic cells than fibrocytes (10,000 dendritic cells versus 3750 fibrocytes) were required to achieve this level of proliferative activity. Interestingly, an inhibition of T cell stimulatory activity with higher APC numbers was observed with monocytes and fibrocytes, but not with dendritic cells.

Figure 6:
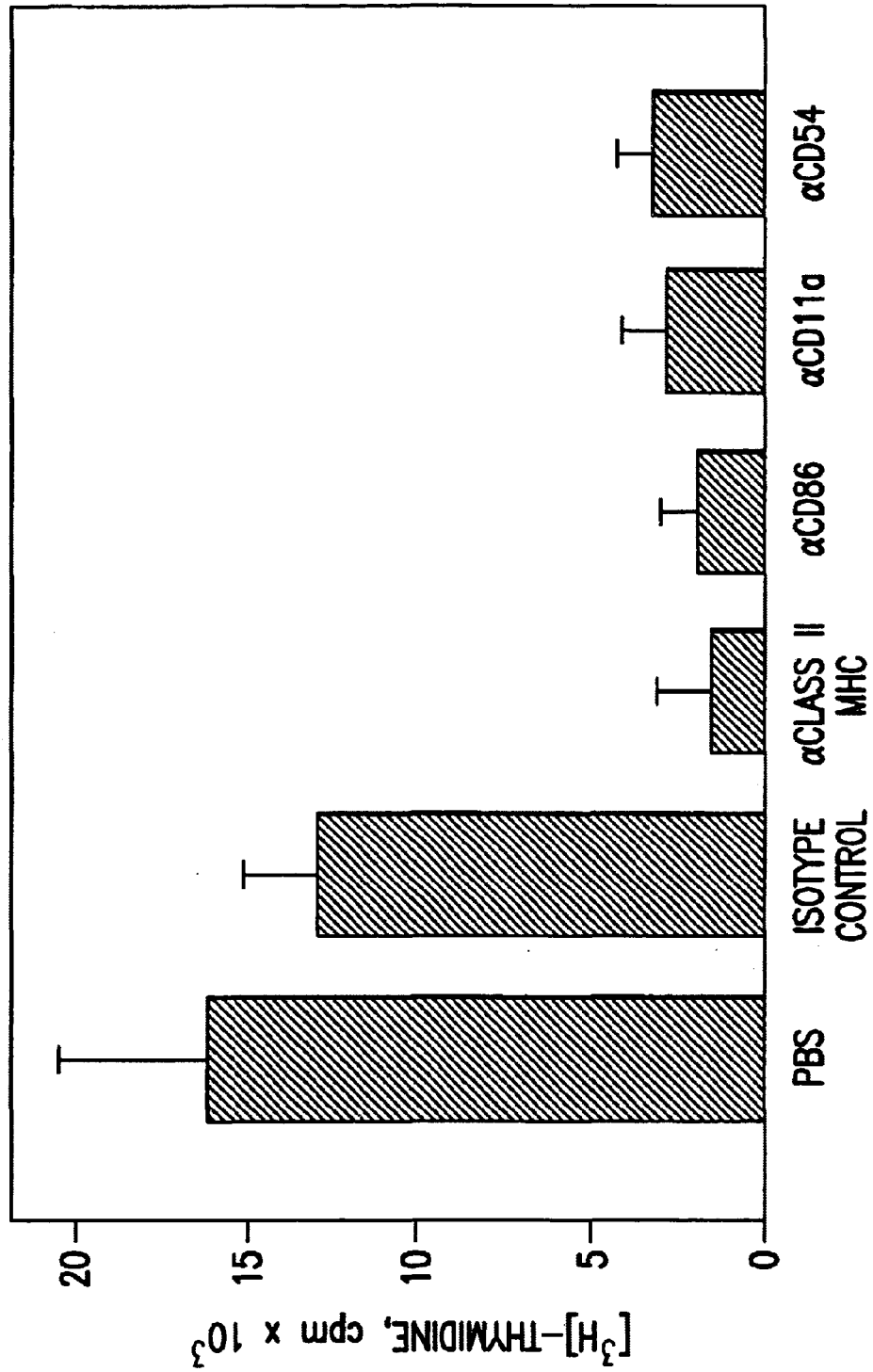
FIG. 6 shows an effect of neutralizing anti-HLA-DR, anti-CD86, anti-CD54, or anti-CD11a mAbs on fibrocyte antigen presentation in vitro. 5 μg/ml of receptor specific or isotype control mAb was added to a 20:1 autologous T-cell:fibrocyte co-incubation prior to the addition of tetanus toxoid. Data are expressed as mean±SD.
Figure 7A:
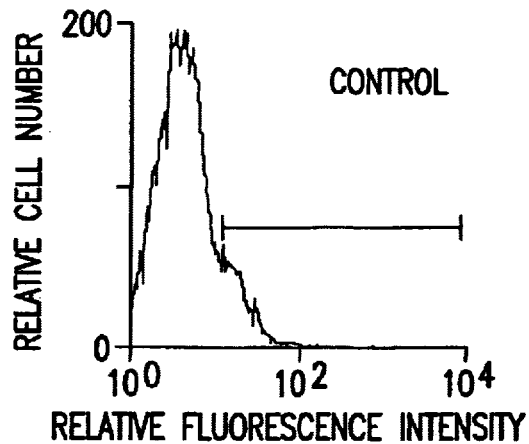
FIG. 7 shows accessory molecule expression by mouse fibrocytes. Murine fibrocytes purified from blood were incubated with phycoerythrin-conjugated (A) or FITC-conjugated (B) mAbs and analyzed by flow cytometry. The horizontal line in each panel marks fluorescence intensity greater than the background staining that was observed with an isotype control mAb.
Figure 7B:
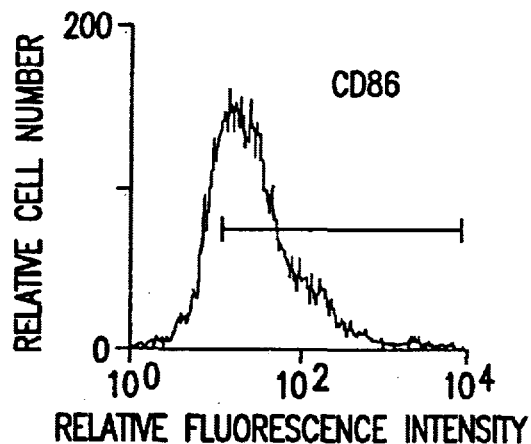
Figure 7C:
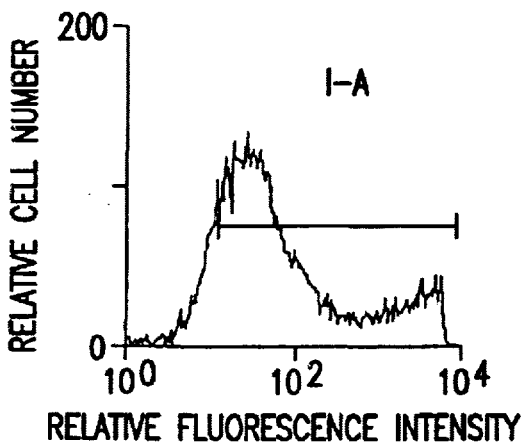
Figure 7D:
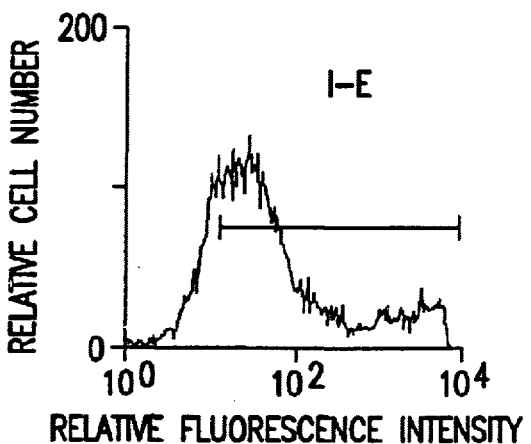
Figure 7E:
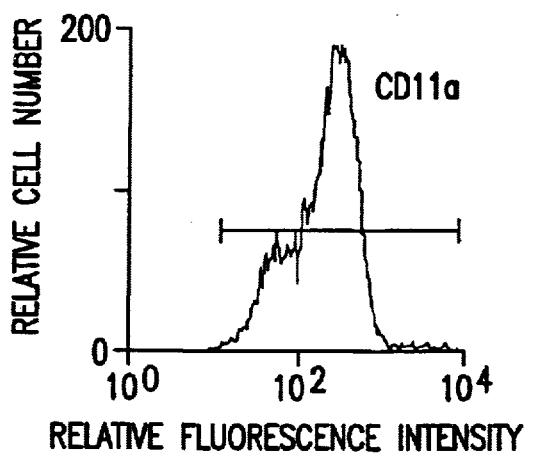
Figure 7F:
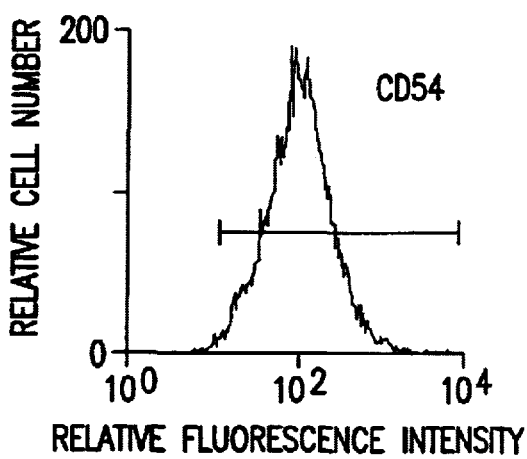

We examined the functional requirement of HLA-DR, CD86, and the co-ligands, CD54 and CD11a, for antigen presentation by human fibrocytes. Neutralizing mAbs were added to the fibrocyte, T cell co-cultures prior to the addition of tetanus toxoid and their effect on antigen-dependent T cell proliferation measured. The effect of the following neutralizing mAbs on fibrocyte antigen presentation was determined: anti-CD11a, anti-CD54, anti-CD86; and anti-HLA-DR. The helper assay was conducted as described above except that 5 mg/ml of receptor-specific or isotype control mAb was added to a 20:1 T cell:fibroctye co-incubation just prior to the addition of tetanus toxoid. Control studies established that these accessory cell receptor-specific mAbs have no effect on human T cell proliferation induced by phorbol 12-myristate 13-acetate (1 ng/ml) plus ionomycin (5 ng/ml) (Sigma). As shown in FIG. 6, fibrocyte-induced T cell proliferation was inhibited significantly by neutralizing mAbs to HLA-DR, CD86, CD11a, or CD54. Taken together, these data indicate that fibrocyte antigen presentation is class II MHC dependent and requires both co-stimulation through CD86 and adhesion through a CD11a:CD54 interaction.

EXAMPLE 3

Figure 8B:
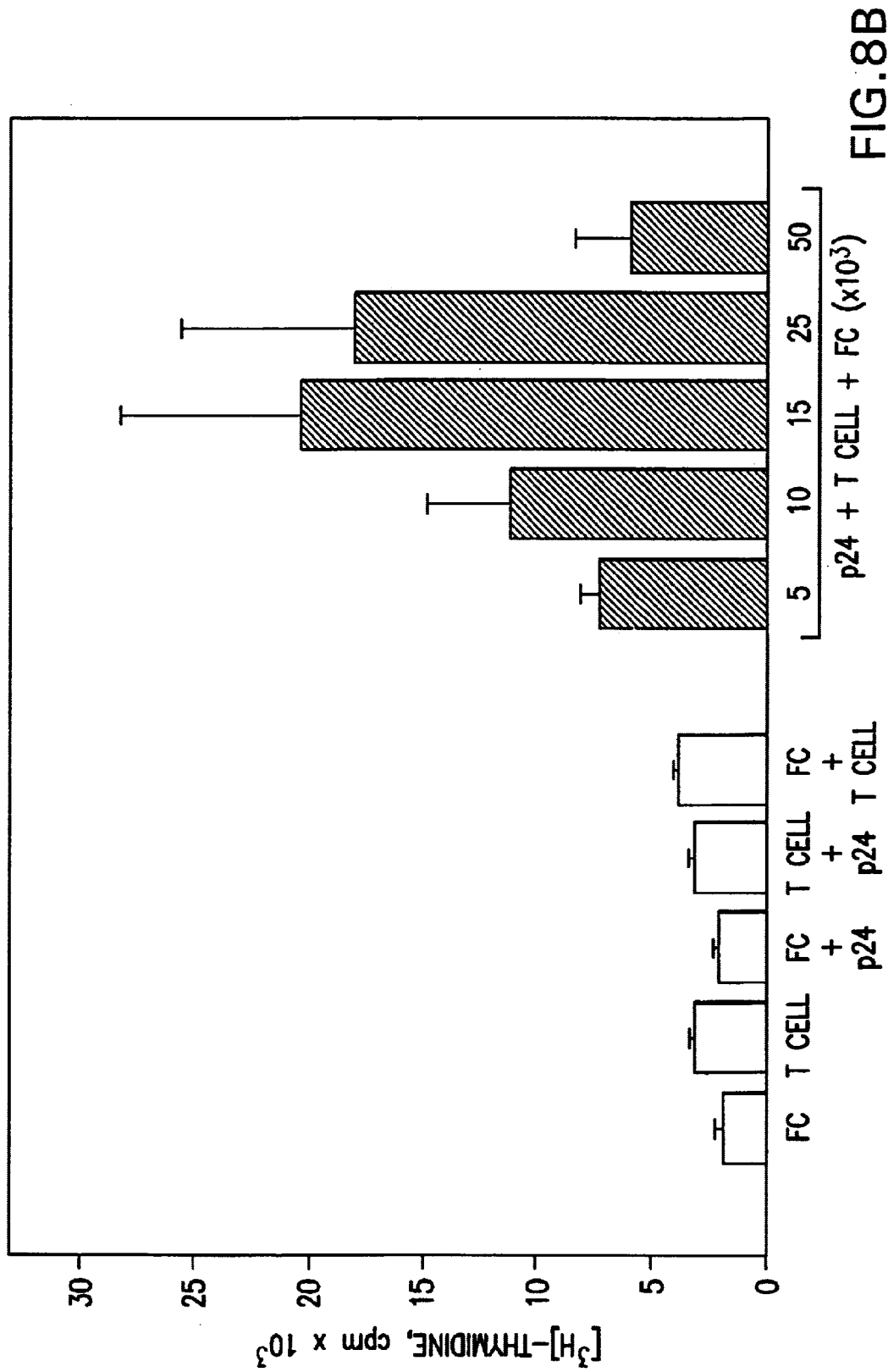

This example illustrates that mouse fibrocytes induced a significant antigen-dependent T cell proliferation response when co-incubated with primed, autologous T cells. T cells were purified from the peripheral blood of BALB/c mice immunized with the HIV proteins p24 and gp120 and stimulated in vitro with p24 or gp120 utilizing fibrocytes as APCs (FIG. 8). BALB/c mice were immunized by i.p. injection of 100 mg of native p24 or gp120 (purified from HIV-1$_{IIIB}$ infected H9 cells, Advanced Biotechnologies, Columbia, Md.) emulsified at 1 mg/ml with Freund's complete adjuvant. After 14 days, the T cells were purified from spleens by chromatography over a T cell enrichment column (R&D Systems, Minneapolis, Minn.). Mouse fibrocytes were purified from peripheral blood as described above and treated with 25 mg/ml mitomycin C (Sigma) in RPMI medium containing 10% fetal calf serum (RPMI/10% FCS) for 30 minutes and then washed 5 times with RPMI/10% FCS. For each assay, the T cells ($2 \times 10^5$) were incubated with mitomycin C-treated fibrocytes at various ratios in the presence of 2 mg/ml p24 or gp120 in RPMI/10% FCS (Jasmes, 1991 infra.). After 5 days of co-culture, the proliferative activity was measured over 12 hours by the incorporation of [$^3$H]thymidine (4 mCi/ml) into DNA as measured by liquid scintillation counting. Controls that were included in each experiment were fibrocytes alone, T cells alone, fibrocytes+antigen, T cells+antigen, and fibrocytes+T cells.

T cell proliferation, as measured by [$^3$H]thymidine incorporation, was greatest when 15,000 murine fibrocytes were co-incubated with $2 \times 10^5$ T cells (p24: 22272±7751 cpm, and gp120: 24276±2680).

Although several cell types have been shown to be capable of presenting antigen to memory T cells, the priming of naive T cells has been considered to be a specialized function of "professional" APCs, particularly dendritic cells (James, 1991 infra.; Levin et al., *J. Immunol.* 12:6742–6750, 1993). To test the ability of mouse fibrocytes to prime naive lymph node T cells in vivo, we pulsed mouse fibrocytes with p24 or gp120 in vitro and injected them intra-dermally into the rear foot pad of unprimed BALB/c mice. Five days later, the popliteal lymph nodes were removed and the constituent cells tested for a re-stimulation proliferative response. Purified BALB/c fibrocytes were cultured for 3 days with 50 mg/ml of p2$^4$ or gp120 in DME/20% FCS, washed 5× in PBS, and injected intra-dermally ($5 \times 10^4$ cells in 20 ml PBS) into the right rear footpad. The proximal popiteal lymph nodes were explanted 5 days later and cell suspensions prepared by teasing with fine forceps. $2 \times 10^5$ lymph node cells/well were cultured with 50 mg/ml of antigen in Click's medium (Gibco) supplemented with 1% heat-inactivated mouse serum (Sigma) and 50 mM 2-mercaptoethanol (Sigma) for 72 hours. The proliferative activity was measured over the last 12 hours of culture by the incorporation of [$^3$H]thymidine (4 mCi/ml) into DNA. Proliferating cells were identified to be primarily CD4$^+$ T cells through depletion of CD4$^+$ T cells by immunomagnetic selection (Dynabeads M-450 L3T4, CD4, Dynal) just prior to liquid scintillation counting. In certain experiments, DBA-2×C3H/HeJ F$_1$ mice (H-2$^{dxk}$) were injected with pulsed fibrocytes from either parent strain (DBA-2, H-2 d or C3H/HeJ, H-2$^k$), and 5 days later, the proximal popliteal lymph nodes were isolated and depleted of endogenous class II MHC$^+$ APCs by immunomagnetic selection (Dynabeads M-450 sheep anti-rat IgG, Dynal, anti-murine class II MHC, rat IgG$_{2b}$, clone ER-TR 3, Accurate). $1 \times 10^5$ APC-depleted lymph node cells then were co-cultured with $1 \times 10^5$ mitomycin C-treated F$_1$ or parent spleen cells as APC with or without gp 120 for 72 hours. The proliferative activity was measured as described above.

Figure 9:
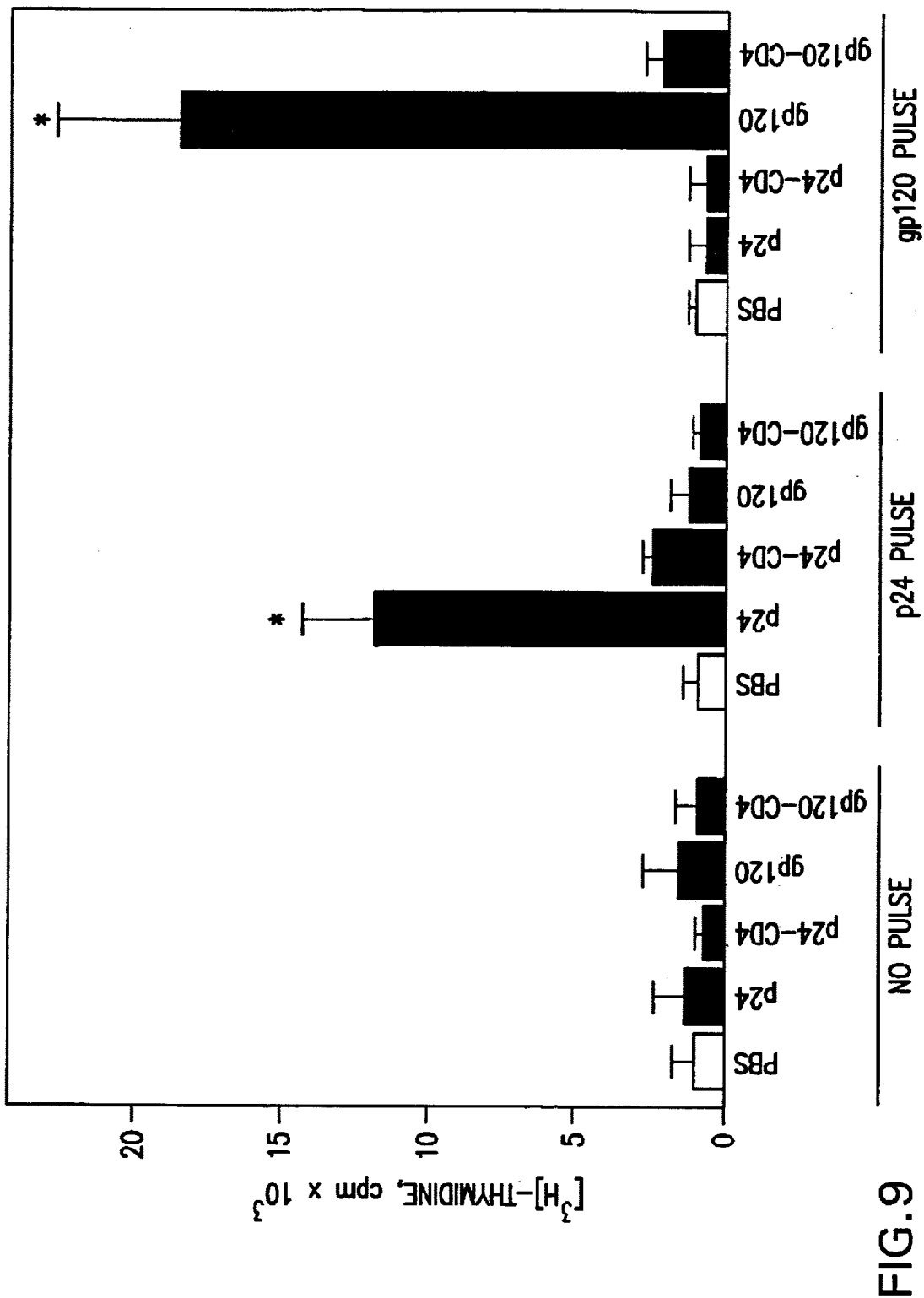
FIG. 9 shows a priming of naive T cells in situ with antigen-pulsed murine fibrocytes. Isolated BALB/c mouse fibrocytes were cultured for 3 days without (NO PULSE), or with 50 mg/ml of p24 (p24 PULSE), or gp120 (gp120 PULSE) in DME/20% FCS, washed, and injected i.d. ($5 \times 10^4$ cells) into the right rear footpad. The proximal popliteal lymph nodes were explanted 5 days later, dissociated, and cultured with PBS or 50 mg/ml of p24 or gp120 for 72 hours. To verify the proliferating cell type, CD4+ T cells were depleted by immunomagnetic selection just prior to liquid scintillation counting (p24-CD4, gp120-CD4). The proliferative activity was measured over the last 12 hours of culture by [$^3$H]thymidine incorporation. Data are expressed as mean±SD and are representative of one experiment that was repeated three times.

Injected, antigen-pulsed fibrocytes thus were found to induce a strong T cell proliferative response (FIG. 9). This response was specific for the priming antigen (p24 or gp120) and consisted predominantly of CD4$^+$ T cells since immunodepletion of this T cell subset resulted in no detectable proliferation signal.

EXAMPLE 4

Figure 10:
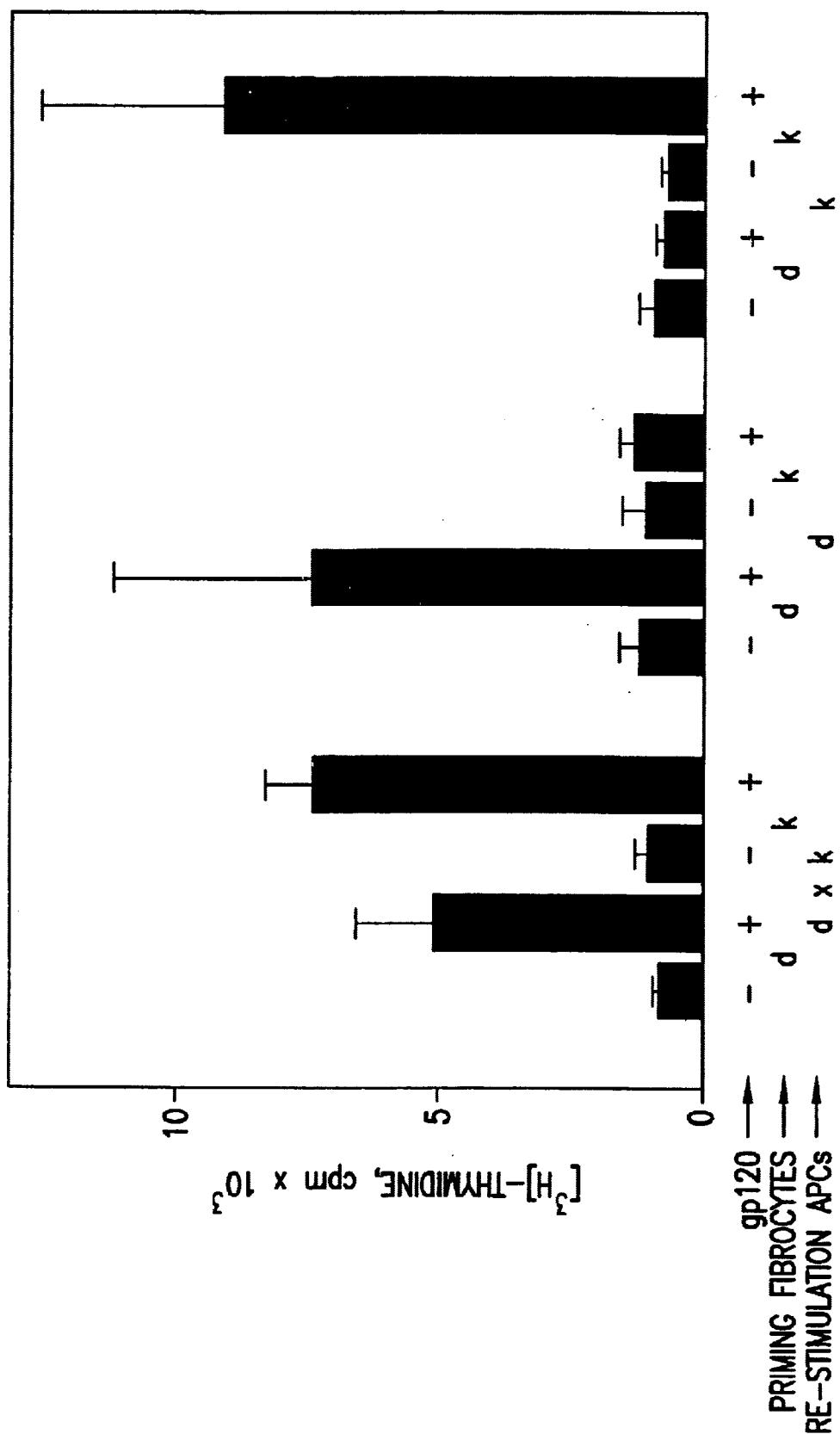
FIG. 10 illustrates a requirement of shared MHC haplotype between priming fibrocyte and re-stimulation APC. DBA-2×C3H/HeJ $F_1$ mice (H-$2^{d\times k}$) were injected with antigen-pulsed fibrocytes from either parent strain DBA-2, H-$2^d$ (d) or C3H/HeJ, H-$2^k$ (k). Five days later, the proximal popliteal lymph node cells were isolated and depleted of endogenous class II MHC+ APCs by immunomagnetic selection. 1×10$^5$ APC-depleted lymph node cells then were co-cultured with 1×10$^5$ mitomycin C-treated $F_1$ (dxk) or parental spleen cells (d or k) as re-stimulation APCs, with or without gp120. The proliferative activity was measured over the last 12 hours of culture by [$^3$H]thymidine incorporation. Data are expressed as mean±SD and are representative of one experiment that was performed three times.

This example illustrates antigen-pulsed fibrocytes were not simply transferring antigen to other host APC types. This example provides the results of experiments in which antigen-pulsed fibrocytes from two parent mouse strains were injected into F$_1$ offspring mice. The T cell reactivity of F$_1$ offspring was confined predominantly to antigens presented by one of the parental strains, and the priming and re-stimulation APCs must necessarily share the same haplotype (Inaba et al., *J. Exp. Med.* 172:631–640, 1990; Sprent, *J. Exp. Med.* 147:1142–1158, 1978. DBA2×C3H/HeJ F$_1$ mice (H-2$^{dxk}$) were injected with pulsed fibrocytes from either parent (DBA-2, H-2$^d$ or C3H/HeJ, H-2$^k$) and, five days later, the proximal popliteal lymph nodes were isolated and depleted of endogenous class II MHC$^+$ APCs by immunomagnetic selection. The F$_1$ APC-depleted lymph node cells were cultured with F$_1$ (H-$_2$dxk) or parent strain (H-2$^d$ or H-2$^k$) spleen cells as the source of APC, with or without gp120. As shown in FIG. 10, the F$_1$ APC-depleted lymph node cells were reactive to antigen in the presence of the F$_1$ re-stimulation APCs when priming was performed with fibrocytes from either parental strain. However, if a parental strain was used as the source of re-stimulation APCs, the F$_1$ APC-depleted lymph node cells would only proliferate if the priming fibrocytes were from the same parental strain. These data indicate that fibrocyte priming and APC re-stimulation of sensitized T cells occurs only in the setting of a shared MHC haplotype. Thus, fibrocytes do not function merely to deliver antigen to other APCs, but rather act to directly sensitize naive T cells in a MHC-specific manner.

EXAMPLE 5

This example illustrates the migration of fibrocytes from a site of peripheral injury into regional lymph nodes. Fluorescently-labeled murine fibrocytes were administered i.d. into the rear footpads of mice and, 24 hours later, the popliteal lymph nodes were removed, dissociated, and examined by fluorescence microscopy. Mouse fibrocytes purified from peripheral blood were stained with the PKH26-GL red fluorescent cell linker compound (Sigma) following the manufacturer's protocol. Prior to staining, a subset of fibrocytes was fixed in 0.1% glutaraldehyde for 30 minutes at room temperature and washed 3× in PBS, 1% FCS. After staining, the cells were washed 5× in PBS, counted, and assessed for labeling efficiency by fluorescence microscopy (~60% for non-fixed, ~40% for fixed) and viability by trypan blue exclusion (~80% for non-fixed, 0% for fixed). $3 \times 10^4$ labeled cells in 20 ml PBS were administered i.d. into the right rear footpad of BALB/c mice. After 24 hours, the mice were killed by CO$_2$ asphyxiation and the popliteal lymph nodes were removed and the cells dissociated. The entire resultant cell suspension from each lymph node ($3 \times 10^6$ cells in 100 ml PBS) then was examined at 400× by fluorescence microscopy and the labeled cells enumerated (all fields). Data are expressed as mean+SD (n=3).

Approximately 5% of the labeled fibrocytes that were injected were observed in the popliteal lymph node (1567±251 of 30,000 fibrocytes injected, n=3 mice) (FIG.

11). By contrast, fibrocytes which were glutaraldehyde-fixed prior to the injection were not observed to migrate into the lymph node (<10 cells (detection limit) of 30,000 fibrocytes injected, n=3 mice).

Additional evidence for a role of fibrocyte antigen presentation in vivo was obtained by immunohistochemical studies of human cutaneous scar specimens. Human cutaneous scar specimens were examined for the presence of spindle-shaped cells that co-expressed CD34 and HLA-DR. Human cutaneous scar tissue specimens were obtained 2–3 weeks after initial injury from individuals without systemic disease. The tissue was fixed in 3.5% paraformaldehyde, sectioned, and processed for immunohistochemical analyses. After blocking endogenous peroxidases with $H_2O_2$ (3%), the deparaffinized sections were incubated with an anti-CD34 mAb (1:50 dilution) (clone QB-END/10) (Accurate, Westbury, N.Y.) or an $IgG_1$ isotype control. After washing, an immunoperoxidase-linked secondary antibody (DAKO, Copenhagen, Denmark) was added, followed by diaminobenzidene as substrate. The sections then were labeled with anti-HLA-DR mAb (Pharmacia) or an $IgG_2b$ isotype control, incubated with an alkaline phosphatase-linked secondary antibody, and developed with new fuchsin (DAKO) as substrate. Control sections stained with an isotype control or without primary antibody showed no immunoreactivity.

Figure 11A:
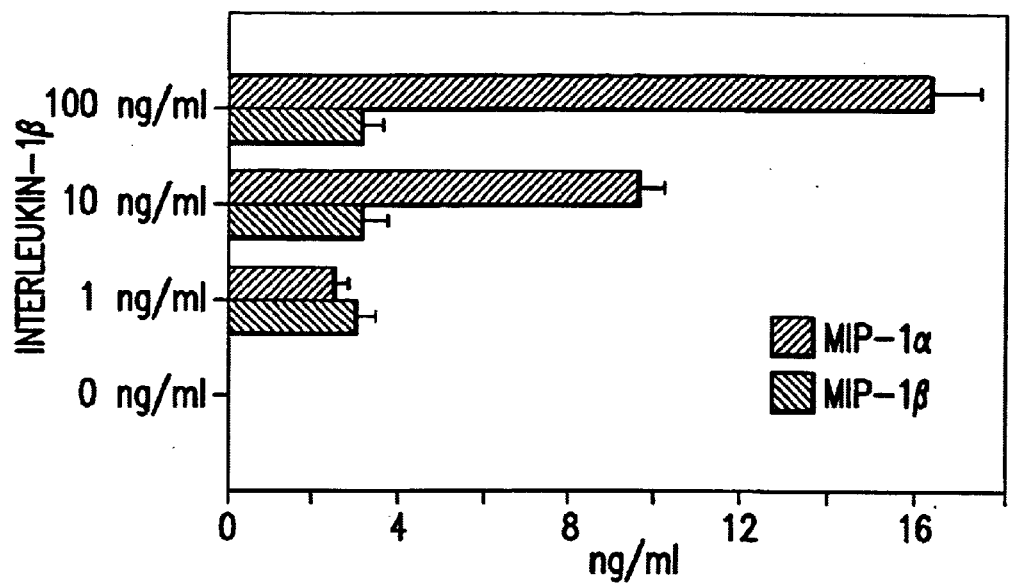
FIG. 11 illustrates an induction of MIP-1α and MIP-1β and bFGF by treatment of fibrocytes with IL-1β.
Figure 11B:
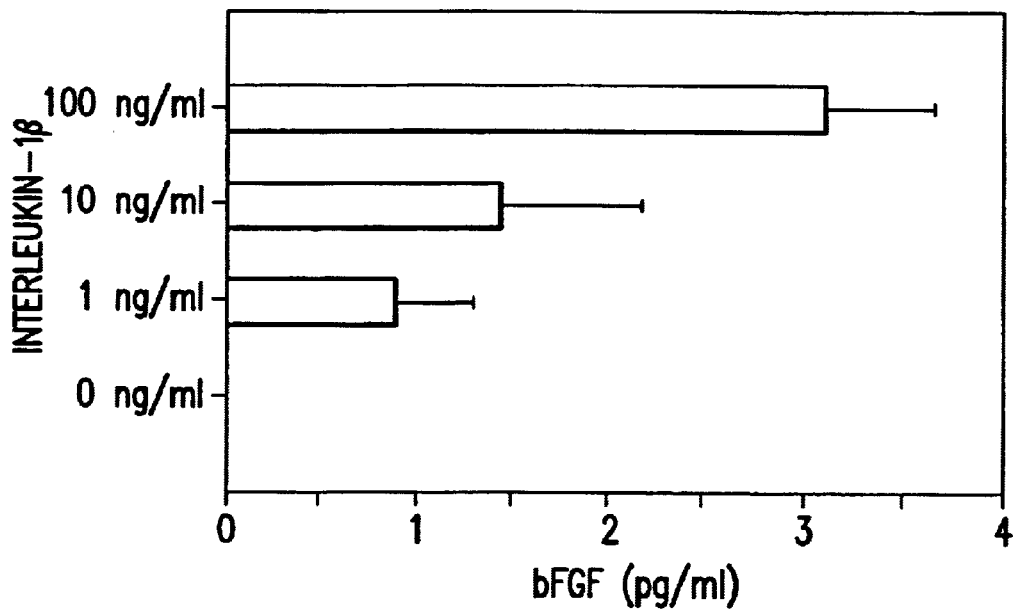
Figure 12:
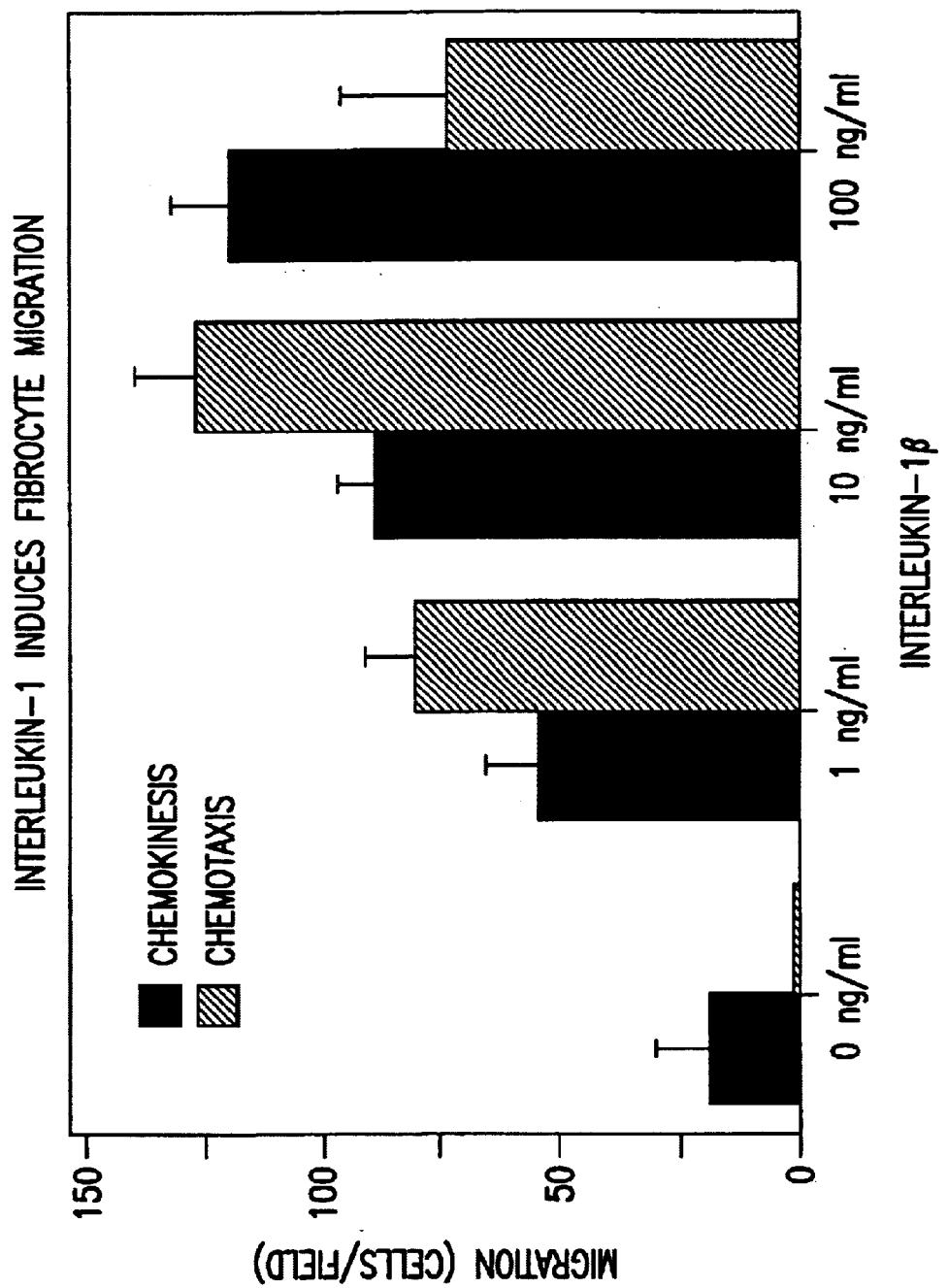
FIG. 12 shows fibrocyte migration in a Boyden Chamber chemotaxis assay induced with treatment with IL-1β.
Figure 13:
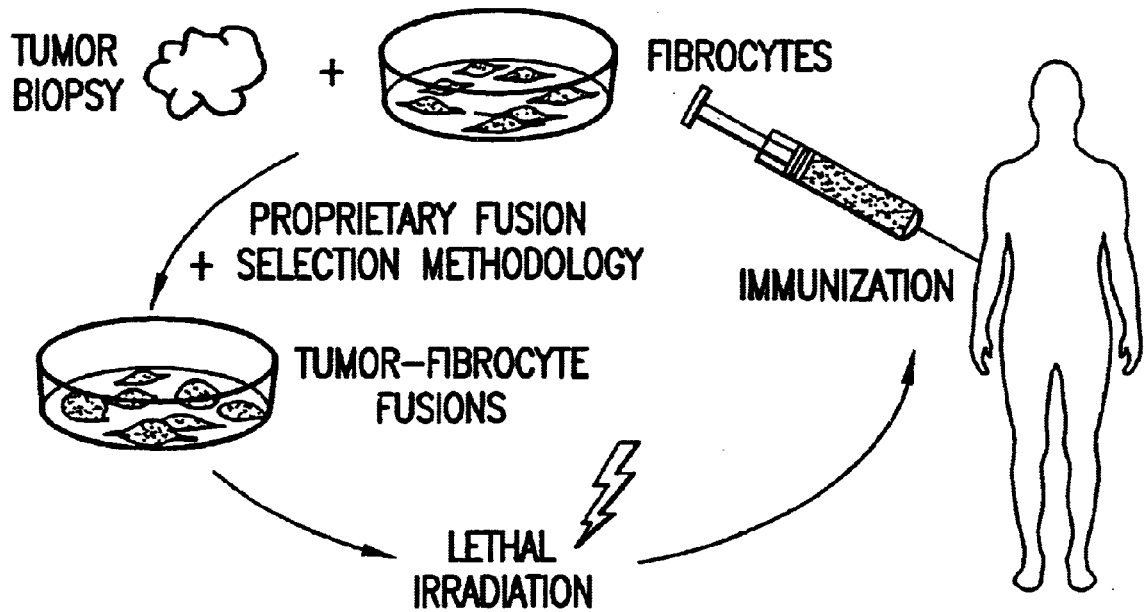
FIG. 13 shows a schematic representation of the use of fibrocytes for tumor immunotherapy in humans.

FIG. 11 shows a sub-dermal region in which numerous connective tissue matrix-associated inflammatory cells were found to stain positively for both CD34 and HLA-DR. Under high power, the expression of both molecules is evident and appears to localize predominantly to cytoplasmic extensions. The expression of HLA-DR by human fibrocytes in vivo suggests that these cells may be active participants in the antigen presentation processes associated with wound repair.

We claim:

1. A fibrocyte-based vaccine formulation comprising isolated fibrocytes having an antigenic component associated therewith, wherein the antigenic component is a tumor antigen selected from the group consisting of pulsed antigen protein, peptide, lipid, carbohydrate or a synthetic antigen thereof, a gene expressing specific tumor antigenic determinants wherein said determinants are proteins or peptides, tumor cells and membrane fragments from tumor cells, wherein the fibrocyte-based vaccine formulation displays at least one tumor antigen of the antipenic component, with the proviso that when the antigenic component is tumor cell or membrane fragments from tumor cells the antigenic component is fused with the isolated fibrocytes to form a fused cell that is the fibrocyte-based vaccine formulation.

2. The fibrocyte-based therapeutic formulation of claim 1 wherein the fusion process occurs ex vivo and the fibrocyte-based therapeutic formulation is administered in vivo.

3. A method for establishing an immune response against a specific tumor antigen by administering a fibrocyte-based vaccine formulation of claim 1.

4. The method of claim 3 wherein the fibrocyte-based vaccine is produced by a process comprising pulsing fibrocytes in culture with a tumor antigen peptide or protein, or transfecting fibrocytes with genes encoding specific tumor antigenic determinants wherein said determinants are peptides or proteins, or by fusing tumor cells or membrane fragments thereof with fibrocytes.

* * * * *

UNITED STATES PATENT AND TRADEMARK OFFICE
CERTIFICATE OF CORRECTION

PATENT NO. : 6,759,036 B1
DATED : July 6, 2004
INVENTOR(S) : Glenn C. Rice et al.

It is certified that error appears in the above-identified patent and that said Letters Patent is hereby corrected as shown below:

Title page, Item [54] and Column 1, lines 1-2,
Title, "FIBROCYTE-BASE VACCINE FORMULATIONS" should read
-- FIBROCYTE-BASED VACCINE FORMULATIONS --

Title page,
Item [56], References Cited, OTHER PUBLICATIONS, "Kobe" reference,
"Kobe " should read "Kuby"; and before "* cited by examiner" insert:
-- Bucala, R., et al., "Circulating Fibrocytes Define a New Leukocyte Subpopulation That Mediates Tissue Repair", Molecular Medicine, Volume 1, pp. 71-81 (1994).
Freudenthal, P.S., et al., "The Distinct Surface of Human Blood Dendritic Cells, As Observed After An Improved Isolation Method", Proc. Natl. Acad. Sci. USA, Volume 87, pp. 7698-7702 (1990).
Chu, T., et al., "The Normal Langerhans Cell and the LCH Cell", Br. J. Cancer, Volume 70, Suppl. XXIII, S4-S10 (1994).
Schall, T.J., et al., "Human Macrophage Inflammatory Protein $\alpha$ (MIP-1$\alpha$) and MIP-1$\beta$ Chemokines Attract Distinct Populations of Lymphocytes", J. Exp. Med., Volume 177, pp. 1821-1825 (1993).
Wahl, L.M., et al., "Inflammation", Wound Healing: Biochemical and Clinical Aspects, Cohen, et al. (eds.), Saunders Company, Philadelphia, pp. 40-62 (1992).
Geppert, T.D., et al., "Antigen Presentation by Interferon-$\gamma$-Treated Endothelial Cells and Fibroblasts: Differential Ability to Function as Antigen-Presenting Cells Despite Comparable Ia Expression", The Journal of Immunology, Volume 135, No. 6, pp. 3750-3762 (1985).
Pober, J.S., et al., "Ia Expression by Vascular Endothelium is Inducible by Activated T Cells and by Human $\gamma$ Interferon", J. Exp. Med., Volume 157, pp. 1339-1353 (1983).
Le Poole, I.C., et al., "A Novel, Antigen-Presenting Function of Melanocytes and Its Possible Relationship to Hypopigmentary Disorders", The Journal of Immunology, Volume 151, No. 12, pp. 7284-7292 (1993).
Inaba, K., et al., "Dendritic Cells Pulsed with Protein Antigens In Vitro Can Prime Antigen-Specific, MHC-Restricted T Cells In Situ", J. Exp. Med., Volume 172, pp. 631-640 (1990).
Levin, D., et al., "Role of Dendritic Cells in the Priming of $CD4^+$ T Lymphocytes to Peptide Antigen In Vivo", The Journal of Immunology, Volume 151, No. 12, pp. 6742-6750 (1993).
Wang, R., et al., "Human Tumor Antigens Recognized by T Lymphocytes: Implications for Cancer Therapy", Journal of Leukocyte Biology, Volume 60, pp. 296-309 (1996).
Bhardwaj, N., et al., "Influenza Virus-Infected Dendritic Cells Stimulate Strong Proliferative and Cytolytic Responses from Human CD8+ T Cells", J. Clin. Invest., Volume 94, pp. 797-807 (1994).

UNITED STATES PATENT AND TRADEMARK OFFICE
CERTIFICATE OF CORRECTION

PATENT NO. : 6,759,036 B1
DATED : July 6, 2004
INVENTOR(S) : Glenn C. Rice et al.

It is certified that error appears in the above-identified patent and that said Letters Patent is hereby corrected as shown below:

Title page (cont'd),
Bender, A., et al., "Inactivated Influenza Virus, when Presented on Dendritic Cells, Elicits Human $CD8^+$ Cytolytic T Cell Responses", J. Exp. Med., Volume 182, pp. 1663-1671 (1995).
Loken, M. R., et al., "Immunofluorescense of Surface Markers", Chapter 5, Flow Cytometry, Ormeron (ed.), Oxford University Press, Oxford, pp. 67-92 (1994).
Clark, E.A., et al., "How B and T Cells Talk to Each Other", Nature, Volume 367, pp. 425-429 (1994).
James, S.P., "Measurement of Basic Immunologic Characteristics of Human Mononuclear Cells", Current Protocols in Immunology, Coligan, et al. (eds), John Wiley and Sons, Inc., New York, pp. 7.10.1-7.11.4 (1994).
Zar, J.H., "Nonparametic Analysis of Variance", Section 11.4, Biostatistical Analysis, Prentice Hall, Englewood Cliffs, New Jersey, pp. 176-179 (1984).
Young J.W., et al., "Accessory Cell Requirements for the Mixed-Leukocyte Reaction and Polyclonal Mitogens, as Studied with a New Technique for Enriching Blood Dendritic Cells", Cellular Immunology, Volume 111, pp. 167-182 (1988).
Sprent, J., "Restricted Helper Function of $F_1$ Hybrid T Cells Positively Selected to Heterologous Erythrocytes in Irradiated Parental Strain Mice", J. Exp. Med., Volume 147, pp. 1142-1158 (1978). --

Column 2,
Line 24, "Epithliial" should read -- epithelial --.
Line 26, "CD 16" should read -- CD16 --.
Line 30, "*Br. J Cancer*" should read -- *Br. J. Cancer* --.
Line 58, "$CD^{4+}$" should read -- $CD4^+$ --.

Column 3,
Line 18, before "SUMMARY OF THE INVENTION" insert:
    -- HLA-DR expression is considered a prerequisite for antigen presentation in vivo (Gepert and Lipsky, *J. Immunol.* 135:3750-3762, 1985) and human fibrocytes participating in cutaneous tissue repair were found to express high levels of HLA-DR in situ. In mice, an appreciable portion (5%) of fibrocytes were found to home to regional lymph nodes after intradermal injection into skin. Fibrocytes function in vivo to capture foreign proteins at sites of tissue injury and to migrate into regional lymph nodes for the purpose of sensitizing naive T cells and/or activating memory T cells. --

Column 4,
Line 52, "gp 120" should read -- gp120 --.

UNITED STATES PATENT AND TRADEMARK OFFICE
CERTIFICATE OF CORRECTION

PATENT NO. : 6,759,036 B1
DATED : July 6, 2004
INVENTOR(S) : Glenn C. Rice et al.

It is certified that error appears in the above-identified patent and that said Letters Patent is hereby corrected as shown below:

Column 6,
Line 49, "of he" should read -- of the --.

Column 10,
Line 38, "TU 169" should read -- TU169 --.

Column 13,
Line 42, "p2$^4$" should read -- p24 --.
Line 57, "H-$_2$$^{dxk}$" should read -- H-2$^{dxk}$ --.
Line 58, "H-2 d" should read -- H-2$^d$ --.
Line 65, "gp 120" should read -- gp120 --.

Column 14,
Line 25, "(H-$_2$dxk)" should read -- (H-2$^{dxk}$) --.
Line 63, "mean+SD" should read -- mean±SD --.

Column 15,
Line 21, "IgG$_2$b" should read -- IgG$_{2b}$ --.

Column 16,
Line 14, "antipenic" should read -- antigenic --.
Line 15, "is tumor" should read -- is a tumor --.
Line 24, "vaccine" should read -- therapeutic --.

Signed and Sealed this

Eighteenth Day of January, 2005

JON W. DUDAS
*Director of the United States Patent and Trademark Office*